US009649385B2

(12) United States Patent
Ashley et al.

(10) Patent No.: US 9,649,385 B2
(45) Date of Patent: May 16, 2017

(54) HYDROGELS WITH BIODEGRADABLE CROSSLINKING

(75) Inventors: Gary W. Ashley, Alameda, CA (US); Daniel V. Santi, San Francisco, CA (US); Jeffrey C. Henise, San Francisco, CA (US)

(73) Assignee: ProLynx LLC, San Francisco, CA (US)

( * ) Notice: Subject to any disclaimer, the term of this patent is extended or adjusted under 35 U.S.C. 154(b) by 18 days.

(21) Appl. No.: 14/343,819

(22) PCT Filed: Sep. 7, 2012

(86) PCT No.: PCT/US2012/054278
§ 371 (c)(1),
(2), (4) Date: May 28, 2014

(87) PCT Pub. No.: WO2013/036847
PCT Pub. Date: Mar. 14, 2013

(65) Prior Publication Data
US 2014/0288190 A1    Sep. 25, 2014

Related U.S. Application Data

(60) Provisional application No. 61/531,990, filed on Sep. 7, 2011.

(51) Int. Cl.
*A61K 47/30* (2006.01)
*A61K 47/34* (2017.01)
(Continued)

(52) U.S. Cl.
CPC ........ *A61K 47/34* (2013.01); *A61K 47/48215* (2013.01); *A61K 47/48784* (2013.01);
(Continued)

(58) Field of Classification Search
None
See application file for complete search history.

(56) References Cited

U.S. PATENT DOCUMENTS

| 6,258,898 B1 | 7/2001 | Rehfuss et al. |
| 2006/0171920 A1 | 8/2006 | Shechter et al. |

(Continued)

FOREIGN PATENT DOCUMENTS

| WO | WO-2006/003014 | 1/2006 |
| WO | WO-2009/158668 | 12/2009 |

(Continued)

OTHER PUBLICATIONS

Lyu et al (Int J Mol Sci 20:4033-4065, 2009).*
(Continued)

*Primary Examiner* — Craig Ricci
(74) *Attorney, Agent, or Firm* — Morrison & Foerster LLP

(57) ABSTRACT

Hydrogels that degrade under appropriate conditions of pH and temperature by virtue of crosslinking compounds that cleave through an elimination reaction are described. The hydrogels may be used for delivery of various agents, such as pharmaceuticals. This invention provides hydrogels that degrade to smaller, soluble components in a non-enzymatic process upon exposure to physiological conditions and to methods to prepare them. The hydrogels are prepared from crosslinking agents that undergo elimination reactions under physiological conditions, thus cleaving the crosslinking agent from the backbone of the hydrogel. The invention also relates to the crosslinking agents themselves and intermediates in forming the hydro gels of the invention. The biodegradable hydro gels prepared according to the methods of the invention may be of use in diverse fields, including biomedical engineering, absorbent materials, and as carriers for drug delivery.

10 Claims, 6 Drawing Sheets

(51) Int. Cl.
  *A61K 47/48* (2006.01)
  *A61L 15/26* (2006.01)
  *A61L 27/18* (2006.01)
  *A61L 27/52* (2006.01)
  *C07C 271/08* (2006.01)

(52) U.S. Cl.
  CPC ............... *A61L 15/26* (2013.01); *A61L 27/18* (2013.01); *A61L 27/52* (2013.01); *C07C 271/08* (2013.01); *C08G 2650/30* (2013.01)

(56) References Cited

U.S. PATENT DOCUMENTS

| 2009/0269406 | A1* | 10/2009 | Panitch | A61K 8/042 424/487 |
| 2010/0240586 | A1 | 9/2010 | Bao et al. | |
| 2010/0267895 | A1 | 10/2010 | Harris et al. | |

FOREIGN PATENT DOCUMENTS

| WO | WO-2010/059883 | 5/2010 |
| WO | WO-2011/140376 | 11/2011 |
| WO | WO-2011/140392 | 11/2011 |
| WO | WO-2011/140393 | 11/2011 |

OTHER PUBLICATIONS

Cadee, et al., "Release of recombinant human interleukin-2 from dextran-based hydrogels," J Control Release (2002) 78:1-13.
Doxorubicin information from the Myeloma Beacon, dated Oct. 15, 2008, retreived from the Internet Nov. 13, 2012, 4 pages.
Hennink, et al., "Novel crosslinking methods to design hydrogels," Adv Drug Del Rev (2002) 54:13-36.
Hoffman, "Hydrogels for biomedical applications," Adv Drug Del Rev (2002) 54:3-12.
International Preliminary Report on Patentability and Written Opinion for PCT/US2012/054278, dated Mar. 12, 2014, 11 pages.
International Search Report for PCT/US2012/054278, mailed Jan. 17, 2013, 4 pages.
Jeong, et al., "Thermogelling biodegradable copolymer aqueous solutions for injectable protein delivery and tissue engineering," Biomacromolecules (2002) 3(4):865-868.
Sawhney et al., "Bioerodible hydrogels based on photopolymerized poly(ethylene glycol)-co-poly($\alpha$-hydroxy acid) diacrylate macromers," Macromolecules (1993) 26:581-587.
Surini, et al., "Release phenomena of insulin from an implantable device composed of a polyion complex of chitosan and sodium hyaluronate," J Control Release (2003) 90(3):291-301.
Supplementary European Search Report for EP 12829900.5, issued Apr. 26, 2016, 7 pages.

* cited by examiner

HYDROGELS WITH BIODEGRADABLE CROSSLINKING

CROSS-REFERENCE TO RELATED APPLICATIONS

This application is the national phase of PCT application PCT/US2012/054278 having an international filing date of 7 Sep. 2012, which claims benefit of U.S. application Ser. No. 61/531,990 filed 7 Sep. 2011. The contents of the above patent applications are incorporated by reference herein in their entirety.

BACKGROUND ART

A hydrogel is a 3-dimensional network of natural or synthetic hydrophilic polymer chains in which water (up to 99%) is the dispersion medium. Fragile macromolecules often require a well-hydrated environment for activity and structural integrity, and the high degree of hydration of a hydrogel may preserve the folding of a protein needed for its bioactivity. The high water content of the hydrogels render the material biocompatible and minimize inflammatory reactions of tissues in contact with the gel, and provide a flexibility comparable to that of living tissue. Hydrogels are thus of interest in biomedical engineering, as absorbent materials for wound dressings and disposable diapers, and as carriers for extended drug release. Hydrogels have been prepared by physical or chemical crosslinking of hydrophilic natural or synthetic polymers.

Examples of hydrogels formed from crosslinking of natural polymers include those formed from hyaluronans, chitosans, collagen, dextran, pectin, polylysine, gelatin or agarose (see: Hennink, W. E., et al., *Adv. Drug Del. Rev.* (2002) 54:13-36; Hoffman, A. S., *Adv. Drug Del. Rev.* (2002) 43:3-12). These hydrogels consist of high-molecular weight polysaccharide or polypeptide chains. Some examples of their use include the encapsulation of recombinant human interleukin-2 in chemically crosslinked dextran-based hydrogels (Cadee, J. A., et al., *J. Control. Release* (2002) 78:1-13) and insulin in an ionically crosslinked chitosan/hyaluronan complex (Surini, S., et al., *J. Control. Release* (2003) 90:291-301).

Examples of hydrogels formed by chemical or physical crosslinking of synthetic polymers include poly(lactic-co-glycolic) acid (PLGA) polymers, (meth)acrylate-oligolactide-PEO-oligolactide-(meth)acrylate, poly(ethylene glycol) (PEO), poly(propylene glycol) (PPO), PEO-PPO-PEO copolymers (Pluronic), poly(phosphazene), poly(methacrylates), poly(N-vinylpyrrolidone), PL(G)A-PEO-PL(G)A copolymers, poly(ethylene imine), and others (see, for example, Hoffman, A. S., *Adv. Drug Del. Rev* (2002) 43:3-12). Examples of protein-polymer encapsulation using such hydrogels include the encapsulation of insulin in physically crosslinked PEG-g-PLGA and PLGA-g-PEG copolymers (Jeong, B., et al., *Biomacromolecules* (2002) 3:865-868) and bovine serum albumin in chemically crosslinked acrylate-PGA-PEO-PGA-acrylate macromonomers (Sawhney A. S., et al., *Macromolecules* (1993) 26:581-587).

Depending on the pore size, degradation of a hydrogel is typically required for release of the encapsulated compounds. Degradation increases the size of the pores to the extent that the drug may diffuse out of the interior of the hydrogel into surrounding body fluids. Degradation is further desirable in order to remove the hydrogel from the body once drug delivery is complete, as surgical removal of the spent hydrogel carrier is often painful. While many of the known hydrogels are theoretically biodegradable, in practice the degradation is uncontrolled and thus unpredictable. Thus, a need exists for new hydrogel materials that biodegrade at a predetermined rate.

In order to effect degradation of the hydrogel, it is helpful to have crosslinking agents that are cleavable under physiological conditions. In one approach, enzymatic cleavage of the crosslinker as a substrate can effect this result. However, dependence on enzymatic degradation results in inter-patient variability as well as differences between in vivo and in vitro results.

The present invention takes advantage of a cleavage mechanism described in a different context—namely drug release from macromolecular carriers which is disclosed, for example in U.S. application US2006/0171920 and in WO2009/158668, WO2011/140393, WO2011/140392 and WO2011/140376. The elimination reaction relies on a modulating group to control the acidity of a proton; ionization of this proton results in release of the drug.

To applicants' knowledge, this mechanism has not been used to establish a cleavable crosslinker for hydrogels which results in the degradation of the gel.

DISCLOSURE OF THE INVENTION

This invention provides hydrogels that degrade to smaller, soluble components in a non-enzymatic process upon exposure to physiological conditions and to methods to prepare them. The hydrogels are prepared from crosslinking agents that undergo elimination reactions under physiological conditions, thus cleaving the crosslinking agent from the backbone of the hydrogel. The invention also relates to the crosslinking agents themselves and intermediates in forming the hydrogels of the invention. The biodegradable hydrogels prepared according to the methods of the invention may be of use in diverse fields, including biomedical engineering, absorbent materials, and as carriers for drug delivery.

Thus, in one aspect, the invention is directed to a hydrogel that is biodegradable under physiological conditions which hydrogel comprises one or more polymers crosslinked by a linker that decomposes by an elimination reaction. More specifically, the hydrogels contain linkers that when disposed in the polymer residues of formula (1):

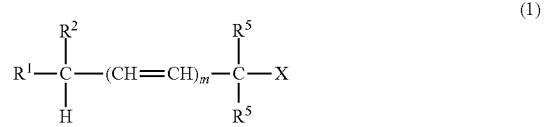

wherein at least one of $R^1$, $R^2$ or $R^5$ along with X is coupled to said one or more polymers.

Alternatively, the linker is a residue of formula (2):

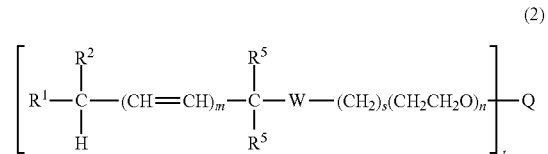

wherein at least two of said $R^1$, $R^2$ or $R^5$ are coupled to one or more polymers.

The definitions of $R^1$, $R^2$, $R^5$, m, X, W, s, n, t, and Q are set forth in detail herein-below. In the case of formula (2), the coupling may be through two $R^1$'s that exist in the same molecule of formula (2) or through one $R^1$ and one $R^5$, for example, in formula (2). That is the requirement that at least two of these substituents as coupled to one or more polymers simply means that in the crosslinker of formula (2) itself, there must be at least two points of attachment. In some embodiments the $R^1$, $R^2$ and $R^5$ substituents are uniform in each of the t "arms".

The hydrogel may further contain one or more drugs. The drug(s) may be simply contained in the pores of the hydrogel, or may be coupled to a crosslinking agent which is in turn coupled to the polymeric backbone of the hydrogel.

The invention also provides methods for preparing biodegradable hydrogels comprising either simultaneously or sequentially contacting at least one reactive polymer and a cleavable crosslinker compound wherein said cleavable crosslinker compound comprises a functional group that reacts with the reactive polymer and a moiety that cleaves by elimination under physiological conditions also comprising a functional group that reacts with one or more polymers. The invention also provides methods for the preparation of drug-releasing biodegradable hydrogels wherein the rates of drug release and of hydrogel biodegradation are controlled.

Thus, the drugs or other agent may simply be entrapped in the hydrogel or may be included in the hydrogel by virtue of coupling through a linker that releases the drug through an elimination reaction as well, without necessity for the degradation of the gel itself.

In another aspect, the invention provides crosslinking reagents comprising a moiety capable of being cleaved by elimination under physiological conditions and further comprising reactive groups capable of forming covalent bonds with reactive polymers.

In still another aspect, the invention provides intermediates formed by reaction of the crosslinking reagents of the invention, with at least one reactive polymer.

MODES OF CARRYING OUT THE INVENTION

Figure 1:
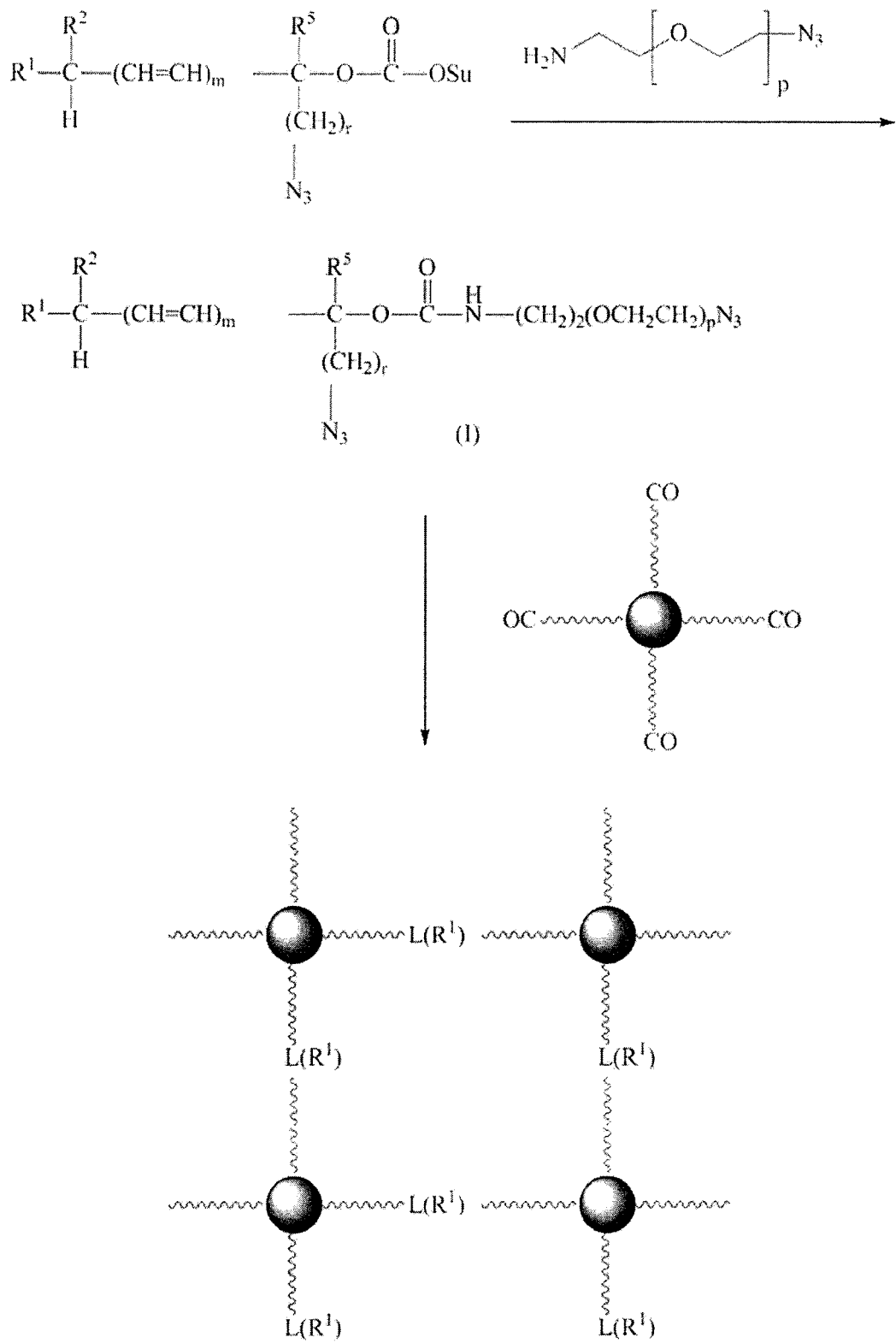
FIG. 1 illustrates one embodiment of the invention wherein hydrogels are formed by crosslinking a multi-arm polymer with a crosslinker of formula (1). A 4-arm polymer wherein each arm is terminated with a cyclooctyne (CO) and a crosslinker of formula (1) wherein one $R^5$ is $(CH_2)_nN_3$ and X is $O-CO-NH-CH_2CH_2(OCH_2CH_2)_p-N_3$ (Example 20) provides a 4×4 hydrogel comprising a beta-eliminative linker L in each crosslink. The degradation rate of the hydrogel is controlled by appropriate choice of the modulating group $R^1$ on linker L. Also illustrated is the formation of (1) by reaction of a succinimidyl carbonate with an amino-PEG-azide.

The hydrogels of the invention are polymer(s) crosslinked by linkers that decouple the polymer(s) by "elimination."

"Elimination" is a reaction mechanism by which a proton H and a leaving group X are removed from a molecule so as to form an alkene. In one embodiment of the invention, the elimination is a 1,2-elimination illustrated as

In other embodiments of the invention, the elimination is a 1,4-elimination illustrated as

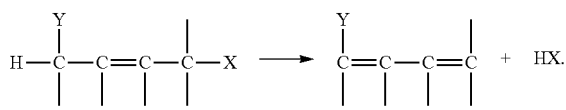

In the elimination mechanism, the illustrated proton H is removed by a base; in aqueous media, the base is typically hydroxide ion such that the rate of elimination is determined by the pH of the medium. Under physiological conditions, the pH of the fluid surrounding and permeating the hydrogel appears to be the predominant factor controlling the rate of elimination. Thus, when X and Y represent chains within a polymer matrix located in a physiological environment, pH-dependent elimination results in disruption of the bond between X and Y and subsequent biodegradation of the polymer matrix in a process which does not require the action of enzymes.

By "a moiety capable of being cleaved by elimination under physiological conditions" is meant a structure comprising a group H—C—(CH=CH)$_m$—C—X wherein m is 0 or 1 and X is a leaving group, wherein an elimination reaction as described above to remove the elements of HX can occur at a rate such that the half-life of the reaction is between 1 and 10,000 hours under physiological conditions of pH and temperature. Preferably, the half-life of the reaction is between 1 and 5,000 hours, and more preferably between 1 and 1,000 hours, under physiological conditions of pH and temperature. By physiological conditions of pH and temperature is meant a pH of between 7 and 8 and a temperature between 30 and 40° C.

It should be noted that when ranges are given in the present application, such as 1-1,000 hours, the intermediate interval numbers should be considered as disclosed as if specifically and explicitly set forth. This avoids the necessity of long list of numbers and applicants clearly intend to include any arbitrary range between the outer boundaries. For example, the range 1-1,000 also includes 1-500 and 2-10.

By hydrogel is meant a three-dimensional, predominantly hydrophilic polymeric network comprising a large quantity of water, formed by chemical or physical crosslinking of natural or synthetic homopolymers, copolymers, or oligomers. Hydrogels may be formed through crosslinking polyethylene glycols (considered to be synonymous with polyethylene oxides), polypropylene glycols, poly(N-vinylpyrrolidone), polymethacrylates, polyphosphazenes, polylactides, polyacrylamides, polyglycolates, polyethylene imines, agarose, dextran, gelatin, collagen, polylysine, chitosans, alginates, hyaluronans, pectin, carrageenan. The polymer may be a multi-armed polymer as illustrated below.

Hydrogels may also be environment-sensitive, for example being liquids at low temperature but gelling at 37° C., for example hydrogels formed from poly(N-isopropylacrylamide).

By mesoporous hydrogel is meant a hydrogel having pores between approximately 1 nm and approximately 100 nm in diameter. The pores in mesoporous hydrogels are sufficiently large to allow for free diffusion of biological molecules such as proteins. By macroporous hydrogel is meant a hydrogel having pores greater than approximately 100 nm in diameter. By microporous hydrogel is meant a hydrogel having pores less than approximately 1 nm in diameter.

By reactive polymer and reactive oligomer is meant a polymer or oligomer comprising functional groups that are reactive towards other functional groups, most preferably under mild conditions compatible with the stability requirements of peptides, proteins, and other biomolecules. Suitable functional groups found in reactive polymers include maleimides, thiols or protected thiols, alcohols, acrylates, acrylamides, amines or protected amines, carboxylic acids or protected carboxylic acids, azides, alkynes including cycloalkynes, 1,3-dienes including cyclopentadienes and furans, alpha-halocarbonyls, and N-hydroxysuccinimidyl, N-hydroxysulfosuccinimidyl, or nitrophenyl esters or carbonates.

By functional group capable of connecting to a reactive polymer is meant a functional group that reacts to a corresponding functional group of a reactive polymer to form a covalent bond to the polymer. Suitable functional groups capable of connecting to a reactive polymer include maleimides, thiols or protected thiols, acrylates, acrylamides, amines or protected amines, carboxylic acids or protected carboxylic acids, azides, alkynes including cycloalkynes, 1,3-dienes including cyclopentadienes and furans, alpha-halocarbonyls, and N-hydroxysuccinimidyl, N-hydroxysulfosuccinimidyl, or nitrophenyl esters or carbonates.

By biodegradable hydrogel is meant a hydrogel that loses its structural integrity through the cleavage of component chemical bonds under physiological conditions of pH and temperature. Biodegradation may be enzymatically catalyzed or may be solely dependent upon environmental factors such as pH and temperature. Biodegradation results in formation of fragments of the polymeric network that are sufficiently small to be soluble and thus undergo clearance from the system through the usual physiological pathways.

By crosslinking reagent is meant a compound comprising at least two functional groups that are capable of forming covalent bonds with one or more reactive polymers or oligomers. Typically, the reactive polymers or oligomers are soluble, and crosslinking results in formation of an insoluble three-dimensional network or gel. The two functional groups of the crosslinking reagent may be identical (homobifunctional) or different (heterobifunctional). The functional groups of the heterobifunctional crosslinking reagent are chosen so as to allow for reaction of one functional group with a cognate group of the reactive polymer or oligomer and reaction of the second functional group with a cognate group of the same or a different reactive polymer or oligomer. The two functional groups of a bifunctional crosslinking reagent are chosen so that they are not reactive with themselves, i.e., are not cognates.

Examples of cognate reactive pairs of functional groups include:
  Azide+acetylene, cyclooctyne, maleimide
  Thiol+maleimide, acrylate, acrylamide, vinylsulfone, vinylsulfonamide, halocarbonyl Amine+carboxylic acid, activated carboxylic acid
Maleimide+1,3-diene, cyclopentadiene, furan Thus, as one example a heterobifunctional crosslinking reagent may be prepared having an azide and an amine group, but not an azide and a cyclooctyne group.

"Substituted" means an alkyl, alkenyl, alkynyl, aryl, or heteroaryl group comprising one or more substituent groups in place of one or more hydrogen atoms. Substituent groups may generally be selected from halogen including F, Cl, Br, and I; lower alkyl including linear, branched, and cyclic; lower haloalkyl including fluoroalkyl, chloroalkyl, bromoalkyl, and iodoalkyl; OH; lower alkoxy including linear, branched, and cyclic; SH; lower alkylthio including linear, branched, and cyclic; amino, alkylamino, dialkylamino, silyl including alkylsilyl, alkoxysilyl, and arylsilyl; nitro; cyano; carbonyl; carboxylic acid, carboxylic ester, carboxylic amide; aminocarbonyl; aminoacyl; carbamate; urea; thiocarbamate; thiourea; ketone; sulfone; sulfonamide; aryl including phenyl, naphthyl, and anthracenyl; heteroaryl including 5-member heteroaryls including as pyrrole, imidazole, furan, thiophene, oxazole, thiazole, isoxazole, isothiazole, thiadiazole, triazole, oxadiazole, and tetrazole, 6-member heteroaryls including pyridine, pyrimidine, pyrazine, and fused heteroaryls including benzofuran, benzothiophene, benzoxazole, benzimidazole, indole, benzothiazole, benzisoxazole, and benzisothiazole.

The properties of $R^1$ and $R^2$ may be modulated by the optional addition of electron-donating or electron-withdrawing substituents. By the term "electron-donating group" is meant a substituent resulting in a decrease in the acidity of the $R^1R^2CH$; electron-donating groups are typically associated with negative Hammett σ or Taft σ* constants and are well-known in the art of physical organic chemistry. (Hammett constants refer to aryl/heteroaryl substituents, Taft constants refer to substituents on non-aromatic moieties). Examples of suitable electron-donating substituents include but are not limited to lower alkyl, lower alkoxy, lower alkylthio, amino, alkylamino, dialkylamino, and silyl. Similarly, by "electron-withdrawing group" is meant a substituent resulting in an increase in the acidity of the $R^1R^2CH$ group; electron-withdrawing groups are typically associated with positive Hammett σ or Taft σ* constants and are well-known in the art of physical organic chemistry. Examples of suitable electron-withdrawing substituents include but are not limited to halogen, difluoromethyl, trifluoromethyl, nitro, cyano, C(=O)—$R^X$, wherein $R^X$ is H, lower alkyl, lower alkoxy, or amino, or $S(O)_mR^Y$, wherein m=1-2 and $R^Y$ is lower alkyl, aryl, or heteroaryl. As is well-known in the art, the electronic influence of a substituent group may depend upon the position of the substituent. For example, an alkoxy substituent on the ortho- or para-position of an aryl ring is electron-donating, and is characterized by a negative Hammett σ constant, while an alkoxy substituent on the meta-position of an aryl ring is electron-withdrawing and is characterized by a positive Hammett σ constant. A table of Hammett σ and Taft σ* constants values is given below.

| Substituent | σ (meta) | σ (para) | σ* |
|---|---|---|---|
| H | 0.00 | 0.00 | 0.49 |
| $CH_3$ | −0.07 | −0.17 | 0 |
| $C_2H_5$ | −0.07 | −0.15 | −0.10 |
| $n\text{-}C_3H_7$ | −0.07 | −0.13 | −0.115 |
| $i\text{-}C_3H_7$ | −0.07 | −0.15 | −0.19 |
| $n\text{-}C_4H_9$ | −0.08 | −0.16 | −0.13 |

-continued

| Substituent | σ (meta) | σ (para) | σ* |
|---|---|---|---|
| $t\text{-}C_4H_9$ | −0.10 | −0.20 | −0.30 |
| $H_2C=CH$ | 0.05 | −0.02 | 0.56 |
| $C_6H_5$ | 0.06 | −0.01 | 0.60 |
| $CH_2Cl$ | 0.11 | 0.12 | 1.05 |
| $CF_3$ | 0.43 | 0.54 | 2.61 |
| CN | 0.56 | 0.66 | 3.30 |
| CHO | 0.35 | 0.42 | |
| $COCH_3$ | 0.38 | 0.50 | 1.65 |
| $CO_2H$ | 0.37 | 0.45 | 2.08 |
| $Si(CH_3)_3$ | −0.04 | −0.07 | −0.81 |
| $CH_2Si(CH_3)_4$ | −0.16 | −0.22 | −0.25 |
| F | 0.34 | 0.06 | 3.21 |
| Cl | 0.37 | 0.23 | 2.96 |
| Br | 0.39 | 0.23 | 2.84 |
| I | 0.35 | 0.18 | 2.46 |
| OH | 0.12 | −0.37 | 1.34 |
| $OCH_3$ | 0.12 | −0.27 | 1.81 |
| $OCH_2CH_3$ | 0.10 | −0.24 | 1.68 |
| $OCF_3$ | 0.40 | 0.35 | |
| SH | 0.25 | 0.15 | 1.68 |
| $SCH_3$ | 0.15 | 0.00 | 1.56 |
| $NO_2$ | 0.71 | 0.78 | 4.0 |
| NO | 0.62 | 0.91 | |
| $NH_2$ | −0.16 | −0.66 | 0.62 |
| NHCHO | 0.19 | 0.00 | |
| $NHCOCH_3$ | 0.07 | −0.15 | 1.40 |
| $N(CH_3)_2$ | −0.15 | −0.83 | 0.32 |
| $N(CH_3)_3^+$ | 0.88 | 0.82 | 4.55 |
| $CCl_3$ | 0.47 | | 2.65 |
| $CO_2CH_3$ | 0.32 | 0.39 | 2.00 |
| $CH_2NO_2$ | | | 1.40 |
| $CH_2CF_3$ | | | 0.92 |
| $CH_2OCH_3$ | | | 0.52 |
| $CH_2Ph$ | | 0.46 | 0.26 |
| Ph | 0.06 | −0.01 | 0.60 |

"Alkyl", "alkenyl", and "alkynyl" include linear, branched or cyclic hydrocarbon groups of 1-8 carbons or 1-6 carbons or 1-4 carbons wherein alkyl is a saturated hydrocarbon, alkenyl includes one or more carbon-carbon double bonds and alkynyl includes one or more carbon-carbon triple bonds. Unless otherwise specified these contain 1-6C.

"Aryl" includes aromatic hydrocarbon groups of 6-18 carbons, preferably 6-10 carbons, including groups such as phenyl, naphthyl, and anthracenyl. "Heteroaryl" includes aromatic rings comprising 3-15 carbons containing at least one N, O or S atom, preferably 3-7 carbons containing at least one N, O or S atom, including groups such as pyrrolyl, pyridyl, pyrimidinyl, imidazolyl, oxazolyl, isoxazolyl, thiazolyl, isothiazolyl, quinolyl, indolyl, indenyl, and similar.

"Halogen" includes fluoro, chloro, bromo and iodo.

"Maleimido" is a group of the formula

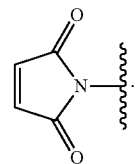 [SMILES: *N1C(=O)C=CC1=O]

The terms "protein" and "peptide" are used interchangeably regardless of chain length, and these terms further include pseudopeptides which comprise linkages other than amide linkages, such as $CH_2NH_2$ linkages as well as peptidomimetics.

The terms "nucleic acids" and "oligonucleotides" are also used interchangeably regardless of chain length. The nucleic acids or oligonucleotides may be single-chain or duplexed or may be DNA, RNA, or modified forms thereof with altered linkages, such as phosphodiesters, phosphoramidates, and the like. For both the proteins and nucleic acids useful as drugs in the invention, these terms also include those with side chains not found in nature in the case of proteins and bases not found in nature in the case of nucleic acids.

Small molecules in the context of drugs is a term well understood in the art, and is meant to include compounds other than proteins and nucleic acids that either are synthesized or are isolated from nature and in general do not resemble proteins or nucleic acids. Typically, they have molecular weights <1,000, although there is no specific cutoff recognized. Nevertheless, the term is well understood in the fields of pharmacology and medicine.

The present invention provides crosslinking reagents comprising a moiety capable of being cleaved by elimination under physiological conditions and further comprising reactive groups capable of forming covalent bonds with reactive polymers. In one embodiment, the crosslinking reagents are of formula (1)

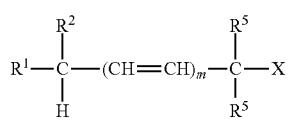

m is 0 or 1;

X comprises a functional group capable of connecting to a reactive polymer that is amenable to elimination from the linker under physiological conditions and a second reactive group $Z^2$ that couples to a reactive polymer;

wherein at least one of $R^1$, $R^2$, and $R^5$ comprises a first functional group $Z^1$ capable of connecting to a polymer;
at least one or both $R^1$ and $R^2$ is independently CN; $NO_2$;
optionally substituted aryl;
optionally substituted heteroaryl;
optionally substituted alkenyl;
optionally substituted alkynyl;
$COR^3$ or $SOR^3$ or $SO_2R^3$ wherein
$R^3$ is H or optionally substituted alkyl;
aryl or arylalkyl, each optionally substituted;
heteroaryl or heteroarylalkyl, each optionally substituted; or
$OR^9$ or $NR^9{}_2$ wherein each $R^9$ is independently H or optionally substituted alkyl, or both $R^9$ groups taken together with the nitrogen to which they are attached form a heterocyclic ring;
$SR^4$ wherein
$R^4$ is optionally substituted alkyl;
aryl or arylalkyl, each optionally substituted; or
heteroaryl or heteroarylalkyl, each optionally substituted;
wherein $R^1$ and $R^2$ may be joined to form a 3-8 membered ring; and
wherein one and only one of $R^1$ and $R^2$ may be H or may be alkyl, arylalkyl or heteroarylalkyl, each optionally substituted; and
each $R^5$ is independently H or is alkyl, alkenylalkyl, alkynylalkyl, $(OCH_2CH_2)_pO$-alkyl, wherein p=1-1000, aryl, arylalkyl, heteroaryl or heteroarylalkyl, each optionally substituted.

The crosslinking reagents of formula (1) comprise a moiety capable of being cleaved by elimination under physiological conditions. Thus, hydrogels formed using crosslinking reagents of formula (1) are biodegradable under physiological conditions. The elimination mechanism is dependent upon the pH and temperature of the medium. While the crosslinking reagents are stable towards cleavage by elimination at low pH and temperature, at physiological values of pH (approximately 7.4) and temperature (approximately 37° C.) the elimination occurs at a rate that is controlled primarily by the $R^1$ and $R^2$ groups, and to a lesser degree by the $R^5$ groups.

The rates of the elimination reaction are predictable based on the structures of the $R^1$, $R^2$, and $R^5$ groups. Electron-withdrawing $R^1$ and $R^2$ groups accelerate the elimination reaction, while electron-donating $R^1$ and $R^2$ groups retard the elimination reaction, such that the rates obtained may be varied so as to provide linkers having half-lives for elimination from minutes to years. Alkyl $R^5$ groups slow the elimination reaction slightly relative to aryl $R^5$ groups. By changing the $R^1$ and $R^2$ groups it is thus possible to control the rate at which the elimination occurs, and consequently the biodegradation rate of the hydrogel can be controlled over a wide range. Hydrogels formed using crosslinking reagents of formula (1) are thus expected to find use in applications where a temporary gel matrix is required, for example as carriers or depots for drug delivery or as temporary scaffolds for tissue regeneration.

Embodiments of X

X comprises a functional group capable of connecting to a reactive polymer and is also amenable to elimination under physiological conditions. Typically, the resulting acid HX will have a $pK_a$ of 10 or less, preferably a $pK_a$ of 8 or less. Examples of suitable X groups thus include carbonates, carbonyl halides, carbamates, thioethers, esters, and optionally substituted phenols. In one embodiment of the invention, X is an activated carbonate such as succinimidyl carbonate, sulfosuccinimidyl carbonate, or nitrophenyl carbonate. In another embodiment of the invention, X is a carbonyl halide such as O(C=O)Cl or O(C=O)F. In another embodiment of the invention, X is a carbamate of the formula

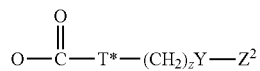

wherein T* is O, S or $NR^6$ wherein $R^6$ is H, optionally substituted alkyl, optionally substituted aryl, optionally substituted heteroaryl, optionally substituted arylalkyl, or optionally substituted heteroarylalkyl; z is 1-6; and Y is absent or is $OR^7$ or $SR^7$, wherein $R^7$ is optionally substituted alkylene, optionally substituted phenylene or $(OCH_2CH_2)_p$, wherein p=1-1000, and $Z^2$ is a functional group capable of connecting with a reactive polymer. In one particular embodiment of the invention, Y is $(OCH_2CH_2)_p$, wherein p=1-1000; or Y is $(OCH_2CH_2)_p$, wherein p=1-100; or Y is $(OCH_2CH_2)_p$, wherein p=1-10.

In another embodiment, X is $OR^7$ or $SR^7$, wherein $R^7$ is optionally substituted alkylene, optionally substituted phenylene or $(OCH_2CH_2)_p$, wherein p=1-1000, and $Z^2$ is a functional group capable of connecting with a reactive polymer.

In certain embodiments, the invention provides crosslinking reagents of formula (1) wherein $R^5$ is the substituent among $R^1$, $R^2$ and $R^5$ that further comprises a functional group capable of connecting to a polymer. In more particular embodiments, the invention provides crosslinking reagents of formula (1) wherein one of $R^5$ further comprises a functional group capable of connecting to a polymer and the other $R^5$ is H.

Thus, the invention provides crosslinking reagents of formula (1a)

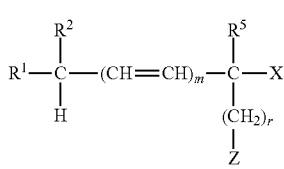
(1a)

wherein m is 0-1; r is 2-8; and $R^1$, $R^2$, $R^5$, m, X, and Z are as defined above. In a more particular embodiment, the invention provides crosslinking reagents of formula (1a) wherein $R^5$ is H. In an even more particular embodiment, the invention provides crosslinking reagents of formula (1a) wherein $R^1$ is CN or $R^8SO_2$, wherein $R^8$ is optionally substituted alkyl, optionally substituted aryl, optionally substituted heteroaryl, or $OR^9$ or $NR^9_2$ wherein each $R^9$ is independently H or optionally substituted alkyl, or both $R^9$ groups taken together with the nitrogen to which they are attached form a heterocyclic ring; $R^2$ and $R^5$ are H, and m=0.

In another embodiment, the invention provides crosslinking reagents of formula (1a) wherein X is of the formula

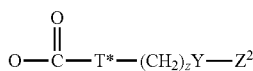

wherein T* is O, S or $NR^6$ wherein $R^6$ is H, optionally substituted alkyl, optionally substituted aryl, optionally substituted heteroaryl, optionally substituted arylalkyl, or optionally substituted heteroarylalkyl; z is 1-6; and Y is absent or is $OR^7$ or $SR^7$, wherein $R^7$ is optionally substituted alkylene, optionally substituted phenylene or $(OCH_2CH_2)_p$, wherein p=1-1000, and $Z^2$ is a functional group capable of connecting with a reactive polymer. In one particular embodiment of the invention, Y is $(OCH_2CH_2)_p$, wherein p=1-1000; or Y is $(OCH_2CH_2)_p$, wherein p=1-100; or Y is $(OCH_2CH_2)_p$, wherein p=1-10.

In another embodiment of the invention, X is $OR^7$ or $SR^7$, wherein $R^7$ is optionally substituted alkylene, optionally substituted phenylene or $(OCH_2CH_2)_p$, wherein p=1-1000, and $Z^2$ is a functional group capable of connecting with a reactive polymer.

In one embodiment, the invention provides crosslinking reagents of formula (1b)

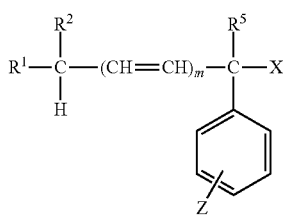
(1b)

wherein m is 0-1 and $R^1$, $R^2$, $R^5$, m, X, and $Z^2$ are as defined above. In a more particular embodiment, the invention provides crosslinking reagents of formula (1b) wherein $R^5$ is H. In an even more particular embodiment, the invention provides crosslinking reagents of formula (1b) wherein $R^1$ is CN or $R^8SO_2$, wherein $R^8$ is optionally substituted alkyl, optionally substituted aryl, optionally substituted heteroaryl, or $OR^9$ or $NR^9_2$ wherein each $R^9$ is independently H or optionally substituted alkyl, or both $R^9$ groups taken together with the nitrogen to which they are attached form a heterocyclic ring; $R^2$ and $R^5$ are H, and m=0.

Methods for preparation of compounds of formula (1) wherein X is OH, Cl, or O-succinimidyl has been previously disclosed in patent publications WO2009/158668, WO2011/140393 and WO2011/140392. Compounds of formula (1) wherein X is a carbamate of the formula

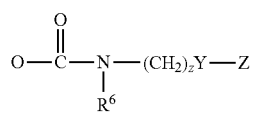

may be prepared from compounds of formula (1) wherein X is Cl or O-succinimidyl by reaction with amines of the formula. $R^6$—NH—$(CH_2)_z$Y—$Z^2$ using methods illustrated in the working examples below.

In another embodiment of the invention, multivalent crosslinking reagents of formula (2) are provided

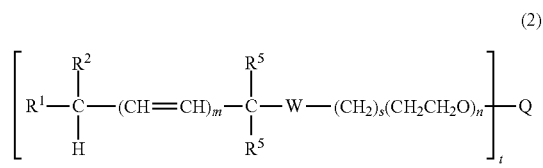
(2)

wherein at least one of $R^1$, $R^2$ and $R^5$ comprises a functional group $Z^1$ capable of connecting to a polymer, and are otherwise defined as in formula (1);

wherein m is 0 or 1;

n is 1-1000;

s is 0-2;

t is 2, 4, 8, 16 or 32,

W is O(C=O)O, O(C=O)NH, O(C=O), S,

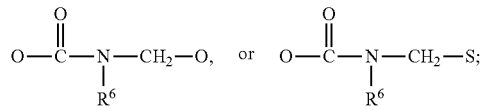

and

Q is a core group having a valency=t, wherein t=2, 4, 8, 16, or 32.

The core group Q is a group of valency=t which connects the multiple arms of the crosslinking reagent. Typical examples of Q include $C(CH_2)_4$ (t=4), wherein the multi-arm reagent is prepared based on a pentaerythritol core; (t=8), wherein the multi-arm reagent is prepared based on a hexaglycerin core; and (t=8), wherein the multi-arm reagent is prepared based on a tripentaerythritol core.

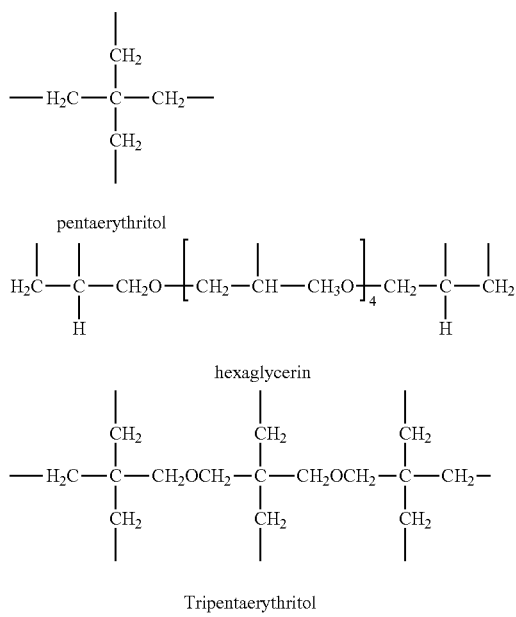

pentaerythritol hexaglycerin

Tripentaerythritol

Compounds of formula (2) may be prepared by the reaction of a multi-arm polyethylene glycol with a reagent of formula (1). A variety of multi-arm polyethyleneglycols are commercially available, for example from NOF Corporation and JenKem Technologies.

In one particular embodiment of the invention, t is 4. In another embodiment of the invention, t is 8.

Preparation of Hydrogels

In another aspect the invention provides methods for preparing biodegradable hydrogels comprising either simultaneously or sequentially contacting at least one reactive polymer and a cleavable crosslinker compound wherein said cleavable crosslinker compound comprises a functional group that reacts with the reactive polymer and a moiety that cleaves by elimination under physiological conditions.

In one embodiment of the invention, biodegradable hydrogels are formed by reaction of a single reactive polymer and a cleavable crosslinker compound wherein said cleavable crosslinker compound comprises a functional group that reacts with the reactive polymer and a moiety also including a functional group that reacts with a reactive polymer that cleaves by elimination under physiological conditions. In this embodiment, the reactive polymer will be multi-valent, so as to allow formation of nodes in the three-dimensional hydrogel matrix. As one illustration of this method, a multi-arm PEG wherein each arm is terminated with a reactive functional group $Z^3$ as defined below is allowed to react with a crosslinker reagent of formula (1) or (2) so as to form a hydrogel. Multi-arm PEGs are commercially available in a variety of sizes and with a variety of reactive functional groups, for example from NOF Corporation and JenKem Technologies. As another illustration of this method, a linear polymer which comprises multiple copies of a reactive functional group $Z^3$ is allowed to react with a crosslinker reagent of formula (1) or (2) so as to form a hydrogel. Illustrations of such linear polymers comprising multiple $Z^3$ groups are hyaluronic acid, carboxymethyl cellulose, polyvinyl alcohol, poly(2-hydroxyethyl methacrylate), dextran, collagen, chitosan, alginate, and agarose.

In another embodiment the invention provides methods for the formation of biodegradable hydrogels through reaction of a first reactive polymer, a second reactive polymer, and a cleavable crosslinker compound that comprises a first functional group that reacts with the first reactive polymer, a second functional group that reacts with the second polymer, and a moiety that cleaves by elimination under physiological conditions. The first and second functional groups may be the same or different. For the formation of a three-dimensional gel network the reactive components (first reactive polymer, second reactive polymer if any) will be multi-armed and thus serve to form nodes in the gel matrix. In preferred embodiments of the invention, this node-forming reactive component comprises at least 3 arms and more preferably at least 4 arms.

In each embodiment the reactive polymers may be homopolymeric or copolymeric polyethylene glycols, polypropylene glycols, poly(N-vinylpyrrolidone), polymethacrylates, polyphosphazenes, polylactides, polyacrylamides, polyglycolates, polyethylene imines, agaroses, dextrans, gelatins, collagens, polylysines, chitosans, alginates, hyaluronans, pectins, or carrageenans that either comprise suitable reactive functionalities in their native state or have been derivatized so as to comprise suitable reactive functionalities. Typical suitable reactive functionalities include maleimides, thiols or protected thiols, alcohols, acrylates, acrylamides, amines or protected amines, carboxylic acids or protected carboxylic acids, azides, alkynes including cycloalkynes, 1,3-dienes including cyclopentadienes and furans, alpha-halocarbonyls, and N-hydroxysuccinimide or N-hydroxysulfosuccinimide esters or carbonates. Native polymers that do not comprise an effective multiplicity of reactive groups can be transformed by reaction with reagents that introduce an effective multiplicity of reactive groups prior to formation of the hydrogel.

In some embodiments, polymers include multivalent branched structures of the formula $[Z^3—(CH_2)_s—(CH_2CH_2O)_n]_tQ$, wherein $Z^3$ is a reactive functional group selected from the options set forth above for $Z^1$ and $Z^2$, s is 0-2, Q is a multivalent core group having valency t, wherein t is 2, 4, 8, 16 or 32. The value of n can be 10-1000 or intermediate values such as 20, 50, 100, etc. This listing is intended to include all intermediate integers between 10 and 1000.

The gel forming reactions may be performed in a variety of suitable solvents, for example water, alcohols, acetonitrile, or tetrahydrofuran, and are preferably performed in aqueous medium.

Formation of the hydrogels may be performed in a stepwise or a concerted fashion. Thus, in one embodiment of the invention, a first reactive polymer is allowed to react with a crosslinking reagent of formula (1) or (2) so as to form an intermediate non-crosslinked combination, which is optionally isolated. This non-crosslinked combination is then allowed to react with the second reactive polymer to form the final crosslinked gel. In another embodiment of the invention, the first reactive polymer, second reactive polymer, and crosslinking reagent of formula (1) or (2) are combined and allowed to react and form the hydrogel in a single operation.

In one embodiment, the invention provides methods for formation of hydrogels by crosslinking a polymer with a crosslinking reagent of formula (1). Depending upon the functionality present, the polymer may be in its native state or may be first derivatized using methods known in the art to introduce functionality that is cross-reactive with the functionality on the compound of formula (1). In this embodiment, the two functional groups capable of reacting with a polymer on the compound of formula (1) are typically the same. An example of this embodiment is illustrated in FIG. 1. As shown, a cleavable crosslinker of Formula (1) with two azide functional groups crosslinks a 4-armed polymer with cyclooctyne functional groups. Alternative gels with other embodiments as noted above for $Z^1$, $Z^2$ and $Z^3$ are prepared to provide similar or identical results.

Figure 2:
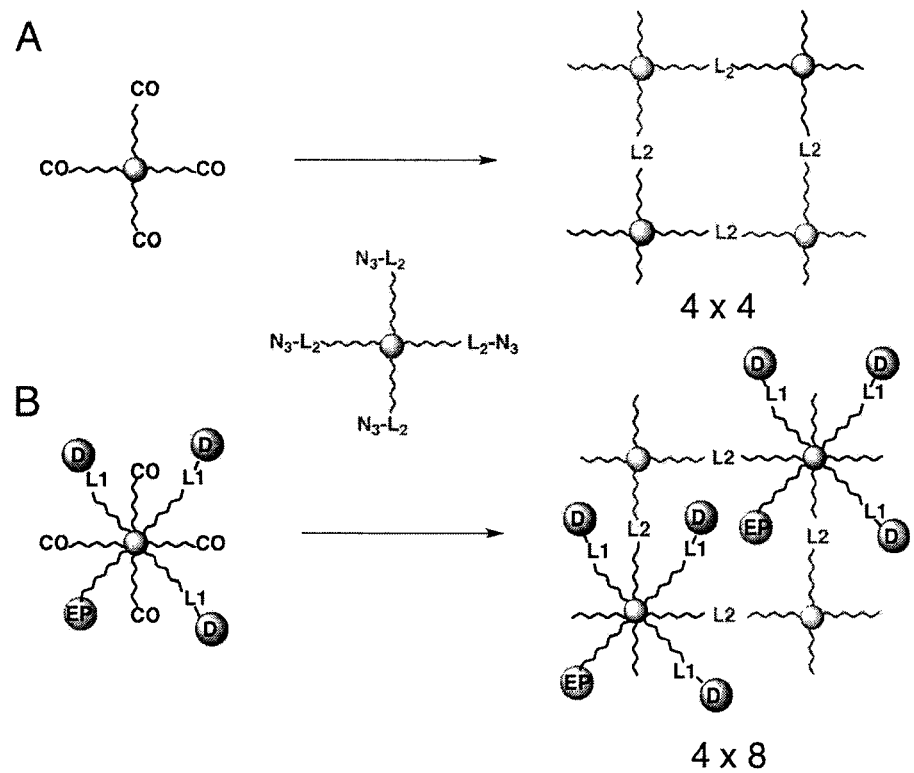
FIGS. 2A and 2B illustrate two embodiments of the invention wherein hydrogels are formed by crosslinking multi-arm polymers with compounds of formula (2). Panel A shows crosslinking a 4-arm polymer wherein each arm is terminated with a cyclooctyne (CO) with another 4-arm polymer of formula (2) wherein each arm is terminated with a beta-eliminative linker azide ($L_2$-$N_3$). The resulting 4×4 hydrogel comprises a beta-eliminative linker in each crosslink. The degradation rate of the hydrogel is controlled by appropriate choice of the linker $L_2$. Panel B shows crosslinking an 8-arm polymer wherein 4 arms are terminated with a cyclooctyne (CO) and the remaining arms are attached to either an erosion probe (EP) or a releasably-linked drug ($L_1$-D). Crosslinking with a 4-arm polymer wherein each arm is terminated with a beta-eliminative linker azide ($L_2$-$N_3$) provides a 4×8 hydrogel comprising a beta-eliminative linker $L_2$ in each crosslink and comprising drug D covalently attached through another beta-eliminative linker $L_1$. The rates of drug release from the hydrogel and hydrogel degradation are controlled by appropriate choices of the linkers $L_1$ and $L_2$, respectively.

In another embodiment, the invention provides methods for formation of hydrogels by crosslinking two differently substituted polymers one of which comprises a crosslinker susceptible to elimination. Two examples of this embodiment are illustrated in FIG. 2. Panel A shows crosslinking a first 4-arm polymer wherein each arm is terminated with a cyclooctyne (CO) with a second 4-arm polymer wherein each arm is terminated with a beta-eliminative linker azide compound of formula (1) ($L_2$-$N_3$) which is thus a 4-arm compound of formula (2). The resulting 4×4 hydrogel comprises a beta-eliminative linker in each crosslink. The gel thus contains alternating nodes derived from the 4-arm polymer and from Formula (2).

As illustrated in Panel B, this method may also use polymers with a greater number of arms. As shown, some of the arms of the 8-armed polymer may be derivatized to a drug through coupling to a compound of formula (3) shown below. In addition, or instead, one or more of the arms may be coupled to a marker compound, such as a fluorescent dye in order to evaluate the rate of disintegration of the gel as a function of the environmental conditions and/or as a function of the nature of $R^1$, $R^2$ and/or $R^5$. This "erosion probe" permits design of gels with desired disintegration rates.

In one aspect of such design, a drug may be simply included in the pores of the gel by forming the gel in the presence of the drug and the delivery rate of the drug's controlled by appropriate choice of substituents in the crosslinking compounds that result in gel formation.

Gels may also be prepared which contain drug both included in the pores and coupled to the polymer through a linkage as shown in formula (3) below. The rates of release from the linkage and from the pores can then be compared.

In the third alternative, the drug may be supplied simply in the form of formula (3) so that the release rate from the gel is determined solely by the elimination reaction of the drug from the gel.

In another aspect, the invention provides hydrogels that are formed according to the above methods. These hydrogels may comprise a variety of hydrophilic polymers, included as described above native or modified forms of polyethylene glycols, polypropylene glycols, poly(N-vinylpyrrolidone), polymethacrylates, polyphosphazenes, polylactides, polyacrylamides, polyglycolates, polyethylene imines, agaroses, dextrans, gelatins, collagens, polylysines, chitosans, alginates, hyaluronans, pectins, carrageenans, or the multiarmed polymers illustrated, and are characterized by their crosslinking which includes at least one moiety capable of being cleaved by elimination under physiological conditions. These hydrogels are thus biodegradable through a pH-dependent process.

Through appropriate choice of reactants and stoichiometries, the pore size of the resulting hydrogels may be determined. The hydrogels of the invention may be microporous, mesoporous, or macroporous, and may have a range of biodegradation rates that are determined by the nature of the crosslinking reagents used in their preparation.

The hydrogels of the invention may also comprise residual reactive groups that were not consumed in the gelling process, either through the stoichiometry chosen, through incomplete crosslinking, or through incorporation of functional groups that do not participate in the gelling process due to orthogonal reactivity. These residual reactive groups may be used to further modify the resulting hydrogel, for example by covalent attachment of drugs or prodrugs. In one embodiment of the invention, the residual reactive groups are used to attach prodrugs comprising a drug attached to a linker that subsequently releases the drug from the hydrogel matrix. In a more particular embodiment of the invention, release of the drug from the hydrogel matrix occurs via an elimination mechanism. The use of eliminative linkers for drug conjugation is described, for example, in PCT publications WO2009/158668 and WO2011/140393, which are hereby incorporated by reference.

One embodiment of drug-releasing degradable hydrogels of the invention is illustrated in FIG. 2B and exemplified in working Examples 29 and 33 below. Reaction of a subset of the functional groups on a first polymer with a releasable linker-drug, wherein the linker comprises a first modulator group that controls the rate of drug release, provides an intermediate drug-loaded polymer; the residual functional groups are reacted with a crosslinking reagent of formula (1) or (2) comprising a second modulator group that controls the rate of hydrogel degradation to provide a drug-loaded degradable hydrogel. By appropriate selection of the modulator groups present on the drug linker and on the crosslinking reagent, the rates of drug release and of hydrogel degradation can be controlled. In one method of the invention, the first polymer is treated with the linker-drug in a first step; the intermediate drug-loaded polymer is optionally isolated; and the hydrogel is formed by reaction with the crosslinker reagent in a separate step. In a second method of the invention, the first polymer, linker-drug, and crosslinker reagent are combined in a single step. If all reactive functionalities on the polymers are not consumed by either connection to linker-drug or crosslinking, the excess functionalities may optionally be capped by reaction with suitable reagents. For example, excess cyclooctynes may be capped by reaction with short PEG-azides such as azidoheptaethylene glycol.

Thus, in one embodiment of the invention, a method for forming a drug-releasing degradable hydrogels is provided consisting of the steps of:

(a) reacting a first multivalent polymer comprising reactive functionalities with a substoichiometric amount of a linker-drug having the formula (3)

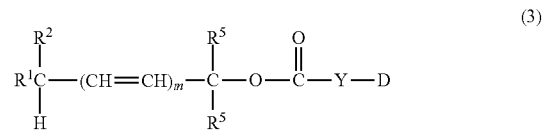

wherein m, $R^1$, $R^2$, and $R^5$ may have the embodiments listed for these in Formulas (1) and (2) although, of course, independently selected, so that a gel that contains both residues of formula (1) or (2) and Formula (3) need not comprise the same substituents of these notations, D is the residue of a drug and Y, in this case, is NH or NBCH$_2$, wherein B is H, alkyl, arylalkyl, heteroaryl, or heteroarylalkyl, each optionally substituted, wherein at least one of $R^1$, $R^2$, $R^5$ is substituted with a functional group corresponding to $Z^1$ reactive with a functional group on the first polymer;

so as to form a drug-loaded first polymer;
(b) optionally isolating the drug-loaded first polymer; and
(c) crosslinking the remaining reactive functionalities on the drug-loaded first polymer with a compound of formula (1) or formula (2) so as to form a hydrogel.

The preparation of linker-drugs of formula (3) is detailed in PCT publications WO2009/158668 and WO/2011/140393, which are hereby incorporated by reference.

The linked drug D may be a small molecule or a polypeptide, including peptides and proteins. Working Example 32 below details the preparation of a drug-releasing degradable hydrogel wherein D is the peptide exenatide, which has the sequence: H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly- Ala-Pro-Pro-Pro-Ser-NH$_2$ (SEQ ID NO:1).

In one embodiment of the invention, the exenatide peptide is coupled to the linker via an amino group to provide

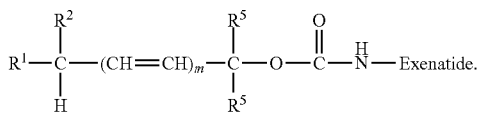

wherein $R^1$, $R^2$, $R^5$, and m are as defined for formula (3) above. In certain embodiments, m=0, $R^2$ is H, one $R^5$ is H, and the other $R^5$ is $(CH_2)_nY$ wherein n=1-6 or $CH_2(OCH_2CH_2)_pY$ wherein p=1-1000 and Y is a group comprising an $N_3$, SH, $S^tBu$, maleimide, 1,3-diene, cyclopentadiene, furan, alkyne, cyclooctyne, acrylate, acrylamide, vinyl sulfone, or vinyl sulfonamide group. In certain embodiments of the invention, $R^1$ is CN or $SO_2R^3$, wherein $R^3$ is optionally substituted alkyl, optionally substituted aryl, optionally substituted heteroaryl, $OR^9$, or $N(R^9)_2$, wherein each $R^9$ is independently H, optionally substituted alkyl, optionally substituted aryl, optionally substituted heteroaryl, and wherein $N(R^9)_2$ may form a heterocyclic ring. The linker may be coupled to any free amino group on the peptide, i.e., the N-terminal amine or any side-chain amine such as the epsilon-amino groups of lysine.

In one specific embodiment of the invention, the linker-drug of formula (3) comprises a reactive azide group on one $R^5$. A substoichiometric amount of the linker-drug is thus reacted with a multi-arm polymer comprising reactive cyclooctyne groups at the terminus of each arm. Examples of reactive cyclooctyne groups include those effective in copper-free 1,3-dipolar cycloaddition reactions with azides, including for example dibenzocyclooctynes, dibenzoazacyclooctynes (DBCO), difluorocyclooctynes (DIFO), and strained bicyclic cyclooctynes such as bicyclononynes (BCN).

Figure 3:
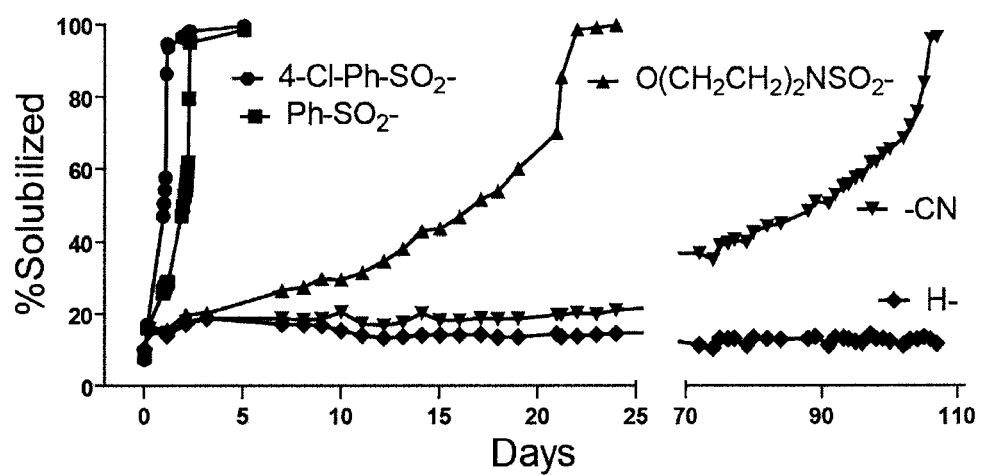
FIG. 3 shows degradation of 4×4 PEG hydrogels at pH 7.4, 37° C. as measured by solubilized fluorescein-PEG fragments described in Example 28; reverse gelation times using different modulators: $R^1$=(4-chlorophenyl)$SO_2$, 30 hrs, $R^1$=phenyl-$SO_2$, 55 hrs; $R^1$=$O(CH_2CH_2)_2NSO_2$, 22 days; $R^1$=CN, 105 days. Solubilized fluorescein was used as erosion probe, with degelation times being defined as the point of complete dissolution.

In one embodiment of the invention, the first polymer comprises at least 8 arms, each arm terminated with a reactive functional group. As shown in FIG. 2B, 3 arms of the first polymer are used for crosslinking to compounds of formula (1) or (2). In a preferred embodiment of the invention, at least 4 arms of the first polymer are used for crosslinking to compounds of formula (1) or (2). Thus, the substoichiometric amount of linker-drug used may range from 0.01 to 5 molar equivalents relative to the first polymer, leading to loading of 0.01 to 5 molecules of drug D per 8-arm first polymer. In one embodiment of the invention, the substoichiometric amount of linker-drug used may range from 0.1 to 5 molar equivalents relative to the first polymer. In another embodiment of the invention, the substoichiometric amount of linker-drug used may range from 1 to 5 molar equivalents relative to the first polymer.

Thus, in certain embodiments of the invention, an exenatide-releasing degradable hydrogel is prepared by reacting a multivalent first polymer comprising a cyclooctyne group at the terminus of each arm with a substoichiometric amount of a linker-drug of formula (4)

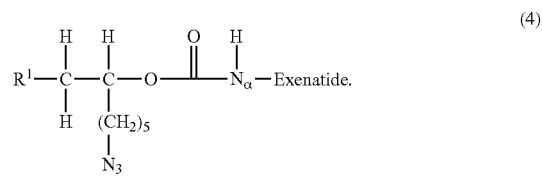

wherein $R^1$=CN; $NO_2$;
optionally substituted aryl;
optionally substituted heteroaryl;
optionally substituted alkenyl;
optionally substituted alkynyl;
$COR^3$ or $SOR^3$ or $SO_2R^3$ wherein
$R^3$ is H or optionally substituted alkyl;
aryl or arylalkyl, each optionally substituted;
heteroaryl or heteroarylalkyl, each optionally substituted; or
$OR^9$ or $NR^9{}_2$ wherein each $R^9$ is independently H or optionally substituted alkyl, or both $R^9$ groups taken together with the nitrogen to which they are attached form a heterocyclic ring; or
$SR^4$ wherein
$R^4$ is optionally substituted alkyl;
aryl or arylalkyl, each optionally substituted; or
heteroaryl or heteroarylalkyl, each optionally substituted;
so as to form an exenatide-loaded first polymer, which is optionally isolated, for example by precipitation, size-exclusion or ion-exchange chromatography, or other methods known in the art. In specific embodiments of the invention, $R^1$ in formula (4) is CN or $SO_2R^3$.

The exenatide-loaded first polymer is then reacted with a cleavable compound of formula (1) or (2) to form the exenatide-releasing degradable hydrogel. In certain embodiments of the invention, the exenatide-releasing first polymer is an 8-arm polyethylene glycol, and the cleavable compound used for hydrogel formation is a compound of formula (2). In certain embodiments of the invention, the cleavable compound used for hydrogel formation is a compound of formula (2) wherein m is 0, n is 10-150, s is 0, t is 4, and Q is $C(CH_2)_4$.

As described above, the rates of drug release and of hydrogel degradation are controlled primarily by choice of the $R^1$ and $R^2$ groups on the drug-linkers and crosslinkers, respectively. The chosen rate of drug release is typically determined by the desired pharmacokinetics of the drug, e.g. the maximal and/or minimal concentrations of free drug over the duration of administration, as has been described in Santi et al PNAS (2012) (submitted) and in co-pending PCT application No. PCT/US2012/054293 (filed 7 Sep. 2012), both of which are hereby incorporated by reference. The $R^1$ and $R^2$ groups on the compounds of formula (I) and (II) are then chosen to provide the optimal rate of hydrogel degradation in order to supply the needed amount of free drug over the duration of administration while minimizing the lifetime of the degradable hydrogel in the body.

Figure 11:
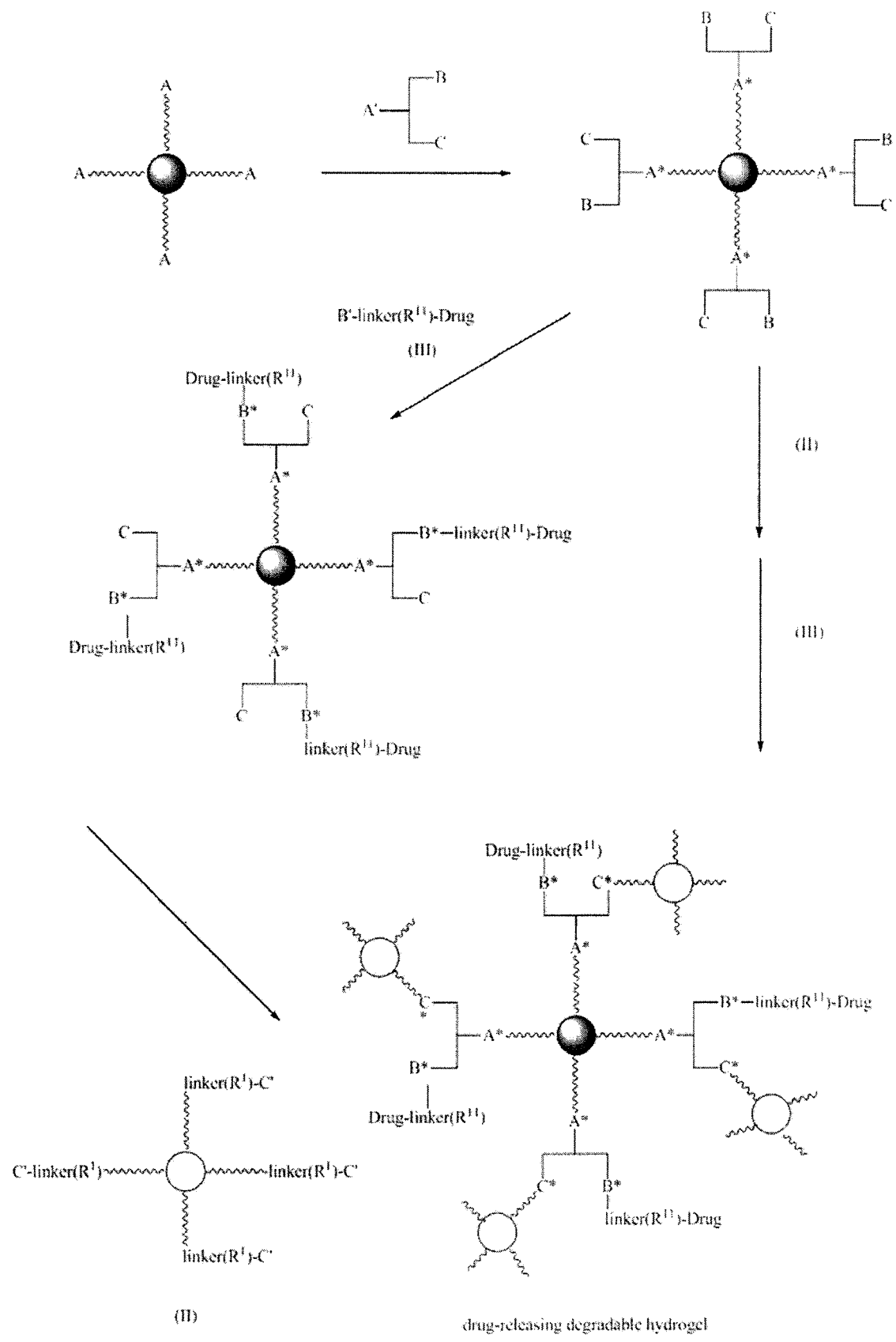
FIG. 11 illustrates an embodiment of the invention wherein drug-releasing hydrogels are formed by reaction of a first polymer comprising at least two orthogonal functional groups (B and C) is reacted with a linker-drug of formula (3) wherein the linker-drug comprises a functional group (B') that reacts with only one of the orthogonal functional groups (B) present on the first polymer, connecting the linker-drug to the first polymer via residue B*. The remaining orthogonal functional group (C) on the resulting drug-loaded first polymer (is used to form a hydrogel by reaction with a compound of formula (1) or (2) wherein these compounds comprise a functional group (C') that reacts with only the remaining orthogonal functional group present on the drug-loaded first polymer to crosslink the hydrogel via residue C*.

In another embodiment of the invention, drug-releasing degradable hydrogels are prepared by a method wherein a multi-arm first polymer wherein each arm is terminated by a group comprising at least two orthogonal functional groups is reacted with a linker-drug of formula (3) wherein the linker-drug comprises a functional group that reacts with only one of the orthogonal functional groups present on the first polymer. The remaining orthogonal functional group on the resulting drug-loaded first polymer is used to form a hydrogel by reaction with a compound of formula (1) or (2) wherein these compounds comprise a functional group that reacts with only one the remaining orthogonal functional groups present on the drug-loaded first polymer. This method is advantageous in that it should provide drug-releasing degradable hydrogels of more regular structure than those formed by stoichiometric control of components. This method is illustrated in working Example 37 below. The multi-arm first polymer wherein each arm is terminated by a group comprising at least two orthogonal functional groups can be prepared from multi-arm polymers wherein each arm terminates with a single functional group by condensation with an appropriate multi-functional adapter. This is illustrated in FIG. 11.

The hydrogels of the invention may be prepared in vitro, then implanted as required. The gels may be cast into specific shapes, or may be prepared as microparticulate or microspherical suspensions for injection. Alternatively, the hydrogels may be formed by in situ gelation, in which case pharmaceutically acceptable formulations of the hydrogel components are prepared; mixing of the components is followed by injection or application prior to gelation. Injection may be subcutaneous, intramuscular, intraocular, intratumoral, or intravenous. The hydrogels of the invention may be applied topically, for example by in situ gelation of the mixed components after application to the skin or to surgical wounds. The hydrogels of the invention may also be applied as coatings on medical devices or surgical dressings.

All references cited herein are hereby incorporated by reference in their entirety. The invention is further illustrated but not limited by the following examples.

Example 1

Preparation of 6-Azidohexanal

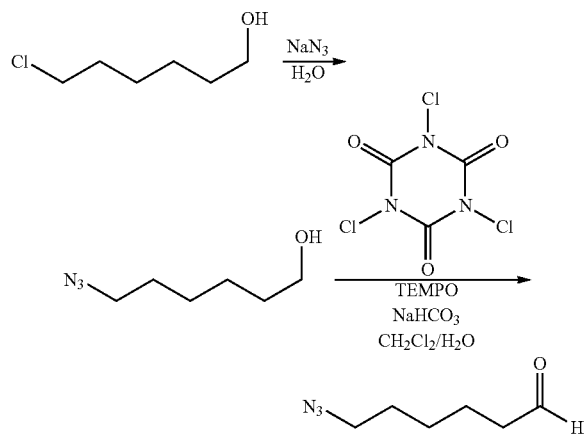

(1) 6-Azido-1-hexanol: a mixture of 6-chloro-1-hexanol (25 g, 183 mmol) and sodium azide (32.5 g, 500 mmol) in 200 mL of water was heated at reflux for 20 h, then cooled to ambient temperature and extracted 3× with ethyl acetate. The combined extracts were washed with brine, dried over MgSO$_4$, filtered, and concentrated to yield the product as a pale yellow oil (28.3 g).

(2) 6-Azidohexanal: Solid trichloroisocyanuric acid (4.3 g) was added in small portions to a vigorously stirred mixture of 6-azido-1-hexanol (7.15 g), TEMPO (50 mg), and sodium bicarbonate (5.0 g) in dichloromethane (100 mL) and water (10 mL). The mixture was stirred for an additional 30 minutes after addition, then filtered through a pad of Celite. The organic phase was separated and washed successively with sat. aq. NaHCO$_3$ and brine, then dried over MgSO$_4$, filtered, and concentrated to provide the product (5.8 g), which was used without further purification.

Example 2

Preparation of ω-Azido-PEG-Aldehydes

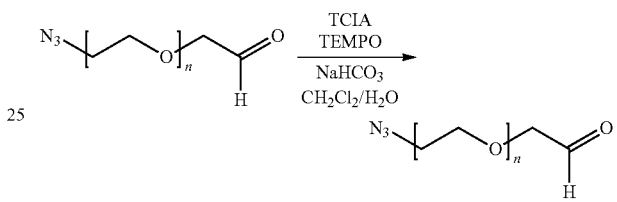

Solid trichloroisocyanuric acid (60 mg) was added to a vigorously stirred mixture of O-(2-azidoethyl)heptaethylene glycol (n=7; 250 mg), 1 mg of TEMPO, 100 mg of NaHCO$_3$, 2 mL of CH$_2$Cl$_2$, and 0.2 mL of water. The mixture turned orange, and after approximately 30 minutes a white suspension was formed. TLC analysis (1:1 acetone/hexane) indicated formation of a product that stained with phosphomolybdic acid. The mixture was diluted with 10 mL of CH$_2$Cl$_2$, dried by stirring with MgSO$_4$, filtered, and evaporated to yield the crude product. This was dissolved in CH$_2$Cl$_2$ and loaded onto a 4-gm column of silica gel equilibrated in hexane, which was eluted sequentially with 25 mL each of hexane, 75:25 hexane/acetone, 50:50 hexane/acetone, and 25:75 hexane/acetone. Product-containing fractions were combined and evaporated to provide the purified product.

Example 3

Preparation of Azidoalcohols

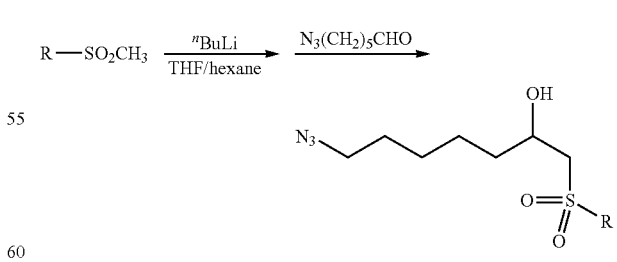

A 1.6 M solution of n-butyllithium (3.1 mL, 5.0 mmol) in hexane was added dropwise to a stirred solution of R—SO$_2$CH$_3$ (5.0 mmol) in anhydrous tetrahydrofuran (THF) (15 mL) cooled to −78° C. After addition, the cooling bath was removed and the mixture was allowed to warm slowly to 0° C. over approximately 30 min. The mixture was then cooled back to −78° C., and 6-azidohexanal (5.5 mmol) was added. After stirring for 15 minutes, the cooling bath was removed and the mixture was allowed to warm. At the point where the mixture became clear, 5 mL of saturated aq. NH₄Cl was added and the mixture was allowed to continue warming to ambient temperature. The mixture was diluted with ethyl acetate and washed successively with water and brine, and then dried over MgSO₄, filtered, and evaporated to provide the crude product as an oil. Chromatography on silica gel using a gradient of ethyl acetate in hexane provided the purified products.

Compounds prepared according to this method include:

1-(4-(trifluoromethyl)phenylsulfonyl)-7-azido-2-heptanol: from 4-(trifluoromethyl)phenyl methyl sulfone (1.73 g, 94%): ¹H-NMR (400 MHz, CDCl₃): δ 8.08 (2H, d, J=8.4-Hz), 7.87 (2H, d, J=8.4-Hz), 4.21 (1H, m), 3.25 (2H, t, J=6.8-Hz), 3.28 (1H, dd, J=8.8, 14.4-Hz), 3.20 (1H, dd, J=2.0, 14.4-Hz), 3.12 (1H, d, J=2.8-Hz), 1.58 (2H, m), 1.5~1.3 (6H, m);

1-(4-chlorophenylsulfonyl)-7-azido-2-heptanol; from 4-chlorophenyl methyl sulfone; colorless oil (1.49 g, 90% yield): ¹H-NMR (400 MHz, d₆-DMSO): δ 7.90 (2H, d, J=8.8-Hz), 7.70 (2H, d, J=8.8-Hz), 4.83 (1H, d, J=6-Hz), 3.86 (1H, m), 3.39 (2H, m), 3.29 (2H, t, J=6.8-Hz), 1.2~1.5 (8H, m);

1-(phenylsulfonyl)-7-azido-2-heptanol; from phenyl methyl sulfone; pale yellow oil (1.25 g, 85%): ¹H-NMR (400 MHz, d₆-DMSO): δ 7.89 (2H, m), 7.72 (1H, m), 7.63 (2H, m), 4.84 (1H, d J=6-Hz), 3.86 (1H, m), 3.33 (2H, m), 3.28 (2H, t, J=6.8-Hz), 1.47 (2H, m), 1.2~1.4 (6H, m);

1-(4-methylphenylsulfonyl)-7-azido-2-heptanol; from 4-(methylsulfonyl)toluene; colorless oil (1.39 g, 85% yield): ¹H-NMR (400 MHz, d₆-DMSO): δ 7.76 (2H, d, J=6.4-Hz), 7.43 (2H, d, J=6.4-Hz), 4.82 (1H, d, J=6-Hz), 3.85 (1H, m), 3.31 (2H, m), 3.28 (2H, t, J=6.8-Hz), 2.41 (3H, s), 1.4~1.5 (2H, m), 1.2~1.4 (6H, m);

1-(4-methoxyphenylsulfonyl)-7-azido-2-heptanol; from 4-methoxyphenyl methyl sulfone (1.53 g, 94% yield): ¹H-NMR (400 MHz, CDCl₃): δ 7.85 (2H, d, J=8.8-Hz), 7.04 (2H, d, J=8.8-Hz), 4.13 (1H, m), 3.90 (3H, s), 3.24 (2H, t, J=6.8-Hz), 3.20 (1H, dd, J=8.8, 14.4-Hz), 3.14 (1H, dd, J=2.4, 14.4-Hz), 2.47 (3H, s), 1.57 (2H, m), 1.5~1.3 (6H, m);

1-(2,4,6-trimethylphenylsulfonyl)-7-azido-2-heptanol; from (2,4,6-trimethyl)phenyl methyl sulfone (1.30 g from 4.0 mmol reaction; 96%): ¹H-NMR (400 MHz, CDCl₃): δ 6.99 (2H, s), 4.30 (1H, m), 3.49 (1H, d, J=2-Hz), 3.25 (2H, t, J=6.8-Hz), 3.18 (1H, d, J=1-Hz), 3.17 (1H, s), 2.66 (6H, s), 2.31 (3H, s), 1.59 (2H, m), 1.5~1.3 (6H, m);

1-(morpholinosulfonyl)-7-azido-2-heptanol; from 1-morpholino methylsulfonamide (1.36 g from 10 mmol reaction, 89%): ¹H-NMR (400 MHz, d₆-DMSO): δ 4.99 (1H, d, J=6.4 Hz), 3.88 (1H, m), 3.62 (4H, t, J=4.8-Hz), 3.32 (2H, t, J=6.8-Hz), 3.20~3.15 (6H, overlap), 1.53 (2H, m), 1.46~1.25 (6H, m); and 1-(methylsulfonyl)-7-azido-2-heptanol; from dimethylsulfone; colorless oil (880 mg, 75%): ¹H-NMR (400 MHz, d₆-DMSO).

Example 4

Preparation of Azidoalcohols

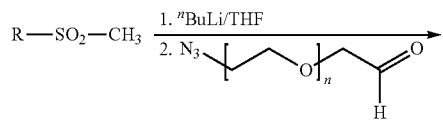

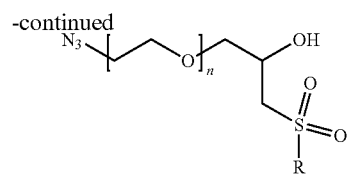

A 1.6 M solution of n-butyllithium (3.1 mL, 5.0 mmol) in hexane is added dropwise to a stirred solution of R—SO₂CH₃ (5.0 mmol) in anhydrous tetrahydrofuran (THF) (15 mL) cooled to −78° C. After addition, the cooling bath is removed and the mixture is allowed to warm slowly to 0° C. over approximately 30 min. The mixture is then cooled back to −78° C., and ω-azido-heptaethylene glycol aldehyde (n=7, 1.2 g) is added. After stirring for 15 minutes, the cooling bath is removed and the mixture is allowed to warm. At the point where the mixture becomes clear, 5 mL of sat. aq. NH₄Cl is added and the mixture is allowed to continue warming to ambient temperature. The mixture was diluted with ethyl acetate and washed successively with water and brine, and then dried over MgSO₄, filtered, and evaporated to provide the crude product. Chromatography on silica gel provides the purified products.

Example 5

Preparation of Azido-Linker Chloroformates

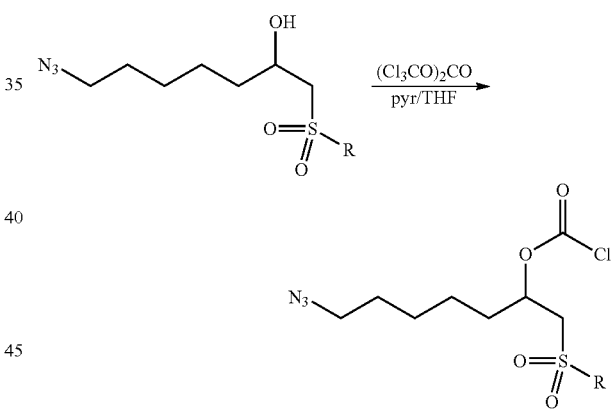

Pyridine (160 μL) was added dropwise to a stirred solution of the azidoalcohol of Example 3 (1.0 mmol) and triphosgene (500 mg) in 15 mL of anhydrous THF. The resulting suspension was stirred for 10 minutes, then filtered and concentrated to provide the crude chloroformate as an oil.

Compounds prepared according to this method include:
1-(4-(trifluoromethyl)phenylsulfonyl)-7-azido-2-heptyl chloroformate
1-(4-chlorophenylsulfonyl)-7-azido-2-heptyl chloroformate;
1-(phenylsulfonyl)-7-azido-2-heptyl chloroformate;
1-(4-methylphenylsulfonyl)-7-azido-2-heptyl chloroformate;
1-(4-methoxyphenylsulfonyl)-7-azido-2-heptyl chloroformate;
1-(2,4,6-trimethylphenylsulfonyl)-7-azido-2-heptyl chloroformate;

1-(4-morpholinosulfonyl)-7-azido-2-heptyl chloroformate; and 1-(methanesulfonyl)-7-azido-2-heptyl chloroformate.

Other chloroformates may be prepared according to this general method.

Example 6

Preparation of Azido-Linker Chloroformates

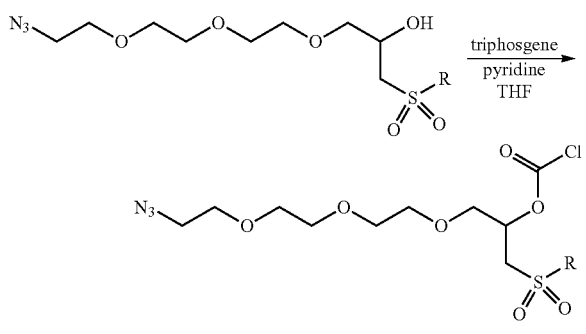

Pyridine (160 µL) is added dropwise to a stirred solution of the azidoalcohol of Example 4 (1.0 mmol) and triphosgene (500 mg) in 15 mL of anhydrous THF. The resulting suspension is stirred for 10 minutes, then filtered and concentrated to provide the crude chloroformate.

Example 7

Preparation of Azido-Linker Succinimidyl Carbonates

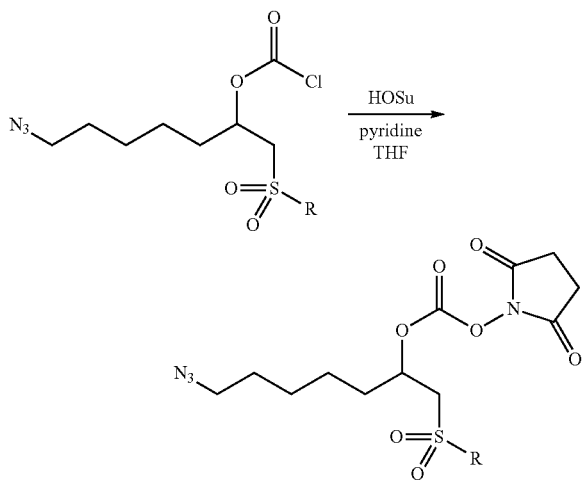

Pyridine (300 µL) was added dropwise to a stirred solution of the chloroformate of Example 5 (1.0 mmol) and N-hydroxysuccinimide (350 mg) in 15 mL of anhydrous THF. The resulting suspension was stirred for 10 minutes, then filtered and concentrated to provide the crude succinimidyl carbonate. Purification by silica gel chromatography provided the purified product as an oil which spontaneously crystallized. Recrystallization could be effected using ethyl acetate/hexane.

Compounds prepared according to this method include:

O-[1-(4-(trifluoromethyl)phenylsulfonyl)-7-azido-2-heptyl]-O'-succinimidyl carbonate: crystals from 40:60 ethyl acetate/hexane (280 mg, 55%): $^1$H-NMR (400 MHz, $d_6$-DMSO): δ 8.12 (2H, m), 8.04 (2H, m), 5.18 (1H, m), 4.15 (1H, dd, J=9.2, 15.2), 3.96 (1H, dd, J=2.4, 15.2), 3.29 (2H, t, J=6.8), 2.80 (4H, s), 1.68 (2H, m), 1.47 (2H, m), 1.27 (4H, m);

O-[1-(4-chlorophenylsulfonyl)-7-azido-2-heptyl]-O'-succinimidyl carbonate: crystals from 40:60 ethyl acetate/hexane (392 mg, 83%): $^1$H-NMR (400 MHz, $d_6$-DMSO): δ 7.85 (2H, m), 7.72 (2H, m), 5.14 (1H, m), 4.04 (1H, dd, J=9.6, 15.6), 3.87 (1H, dd, J=2.4, 15.6), 3.29 (2H, t, J=6.8), 2.81 (4H, s), 1.68 (2H, m), 1.47 (2H, m), 1.27 (4H, m);

O-[1-(phenylsulfonyl)-7-azido-2-heptyl]-O'-succinimidyl carbonate: crystals from 40:60 ethyl acetate/hexanes (391 mg, 89%): $^1$H-NMR (400 MHz, $d_6$-DMSO): δ 7.91 (2H, m), 7.76 (1H, m), 7.66 (2H, m), 5.12 (1H, m), 3.96 (1H, dd, J=8.8, 15.2), 3.83 (1H, dd, J=2.8, 15.2), 3.29 (2H, t, J=6.8), 2.81 (4H, s), 1.69 (2H, m), 1.47 (2H, m), 1.27 (4H, m);

O-[1-(4-methylphenylsulfonyl)-7-azido-2-heptyl]-O'-succinimidyl carbonate: crystals upon standing after chromatography (402 mg, 89%): $^1$H-NMR (400 MHz, $d_6$-DMSO): δ 7.77 (2H, d, J=8.0); 7.45 (2H, d, J=8.0); 5.11 (1H, m), 3.90 (1H, dd, J=8.8, 15.2), 3.79 (1H, dd, J=1.8, 15.2), 3.28 (2H, t, J=6.8), 2.81 (4H, s), 2.41 (3H, s), 1.68 (2H, m), 1.47 (2H, m), 1.27 (4H, m);

O-[1-(4-methoxyphenylsulfonyl)-7-azido-2-heptyl]-O'-succinimidyl carbonate: crystals from 60:40 ethyl acetate/hexane (320 mg, 68%): $^1$H-NMR (400 MHz, $d_6$-DMSO): δ 7.81 (2H, d, J=8.8); 7.15 (2H, d, J=8.8); 5.11 (1H, m), 3.87 (1H, dd, J=8.8, 15.2), 3.86 (3H, s), 3.76 (1H, dd, J=2.8, 15.2), 3.29 (2H, t, J=6.8), 2.80 (4H, s), 1.68 (2H, m), 1.47 (2H, m), 1.27 (4H, m);

O-[1-(2,4,6-trimethylphenylsulfonyl)-7-azido-2-heptyl]-O'-succinimidyl carbonate: colorless oil (458 mg, 95%): $^1$H-NMR (400 MHz, $d_6$-DMSO): δ 7.09 (2H, s), 5.20 (1H, m), 3.82 (1H, dd, J=8.4, 15.2-Hz), 3.67 (1H, dd, J=3.2, 15.2-Hz), 3.30 (2H, t, J=6.8-Hz), 2.79 (4H, s), 2.58 (6H, s), 2.28 (3H, s), 1.75 (2H, m), 1.49 (2H, m), 1.30 (4H, m);

O-[1-(morpholinosulfonyl)-7-azido-2-heptyl]-O'-succinimidyl carbonate: crystals upon standing after chromatography (430 mg, 95%): (400 MHz, CDCl$_3$): δ 5.23 (1H, m), 3.77 (4H, dd, J=4.0, 5.6-Hz), 3.39 (1H, dd, J=6.4, 14.4-Hz), 3.31 (6H, overlap), 3.17 (1H, dd, J=4.8, 14.4-Hz), 2.85 (4H, s), 1.88 (2H, m), 1.61 (2H, m), 1.45 (4H, m); and O-[1-methylsulfonyl-7-azido-2-heptyl]-O'-succinimidyl carbonate: crystals upon standing after chromatography (360 mg, 95%): (400 MHz, CDCl$_3$): δ 5.32 (1H, m), 3.50 (1H, dd, J=7.2, 14.8-Hz), 3.29 (2H, t, J=6.8-Hz), 3.21 (1H, dd, J=0.8, 4.0, 14.8-Hz), 3.02 (3H, s), 2.85 (4H, s), 1.90 (2H, m), 1.62 (2H, m), 1.46 (4H, m).

Other succinimidyl carbonates may be prepared according to this general method.

Example 8

Preparation of Azido-Linker Succinimidyl Carbonates

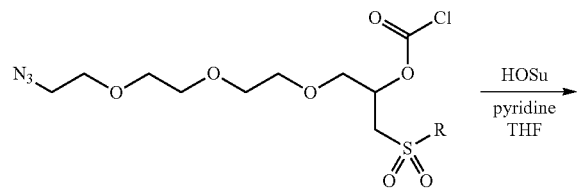

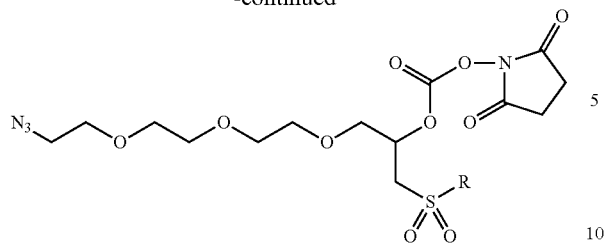

Pyridine (300 μL) is added dropwise to a stirred solution of the chloroformate of Example 6 (1.0 mmol) and N-hydroxysuccinimide (350 mg) in 15 mL of anhydrous THF. The resulting suspension is stirred for 10 minutes, then filtered and concentrated to provide the crude succinimidyl carbonate. Purification by silica gel chromatography provides the purified product.

Example 9

Preparation of Azido-Linker Sulfosuccinimidyl Carbonates

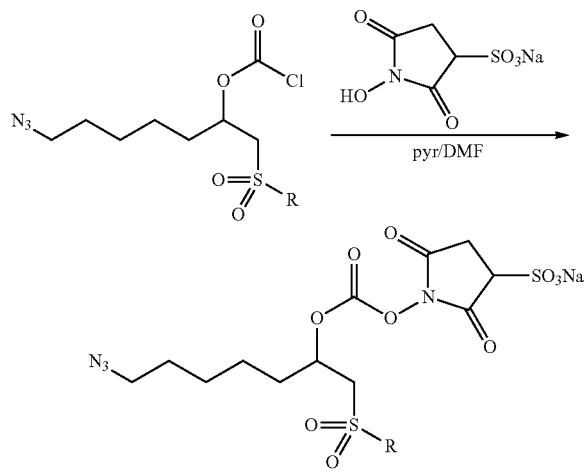

A stirred suspension of sodium N-hydroxysuccinimide sulfonate (1 mmol) in N,N-dimethylformamide (10 mL) is treated with pyridine (3 mmol) and a chloroformate of Example 7. After the suspension clears, the mixture is diluted with ethyl acetate.

Example 10

Preparation of Amino-Linker Alcohols

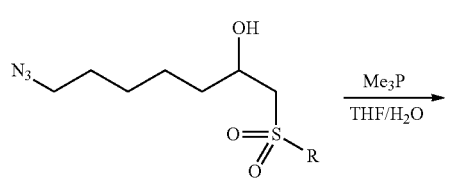

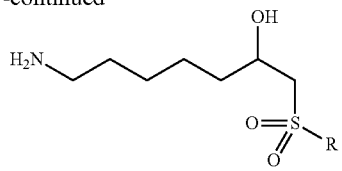

A stirred solution of an azido-linker alcohol of Example 3 (R=phenyl; 1 mmol) in 1 mL of tetrahydrofuran (THF) was treated with a 1.0 M solution of trimethyl-phosphine in THF (1.2 mL) for 1 hour at ambient temperature. Water (0.1 mL) was added, and the mixture was allowed to stir for an additional 1 hour, then the mixture was evaporated to dryness using a rotary evaporator. The residue was dissolved in ethyl acetate, washed with water and brine, then was dried over MgSO$_4$, filtered, and evaporated to provide the product.

Other amino-linker alcohols may be prepared according to this general method.

Example 11

Preparation of $^t$BOC-Amino-Linker Alcohols

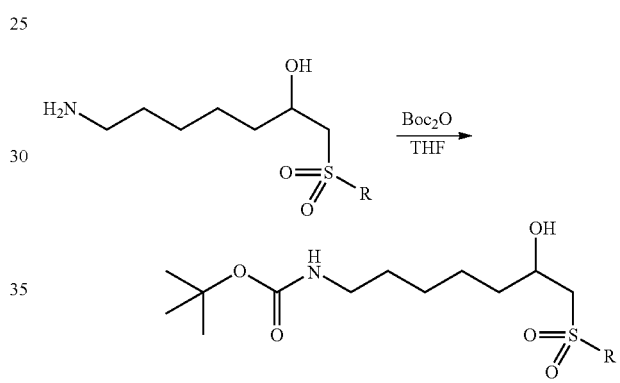

A solution of the amino-linker alcohol of Example 10 (R=phenyl; 1.0 mmol) in 2 mL of THF was treated with di-tert-butyl dicarbonate (1.5 mmol) for 1 hour, and then evaporated to dryness. The residue was dissolved in ethyl acetate, washed with water and brine, then was dried over MgSO$_4$, filtered, and evaporated to provide the product. Chromatography on silica gel using a gradient of ethyl acetate in hexane provided the purified product.

Other $^t$BOC-amino-linker alcohols may be produced according to the same general method.

Example 12

Preparation of 4-(N,N-Diethylcarboxamido)aniline

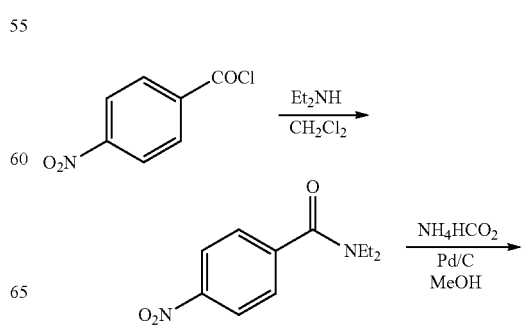

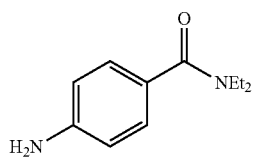

(1) N,N-diethyl 4-nitrobenzamide: Diethylamine (5.6 mL) was added to an ice-cold solution of 4-nitrobenzoyl chloride (5.0 g) in 100 mL of DCM. After 1 h, the mixture was washed successively with water, sat. aq. NaHCO$_3$, and brine, then dried over MgSO$_4$, filtered, and evaporated to provide a colorless liquid that crystallized on standing. Recrystallization from ethyl acetate/hexane provided the product as pale yellow crystals (4.6 g).

(2) 4-(N,N-diethylcarboxamido)aniline: A mixture of N,N-diethyl 4-nitrobenzamide (4.44 g) and 10% palladium on carbon (0.2 g) in 100 mL of methanol was treated with ammonium formate (4.0 g) for 2 h at ambient temperature. The mixture was filtered through Celite and concentrated. The residue was redissolved in DCM, washed successively with 0.5 M Na$_2$CO$_3$, water, and brine, then dried over MgSO$_4$, filtered, and evaporated to provide a crystalline material. Recrystallization from ethyl acetate/hexane provided the product aniline.

Also prepared according to the same procedure was 4-(morpholinocarbonyl)aniline by replacing diethylamine with morpholine.

Example 13

Preparation of Azidocarbamates

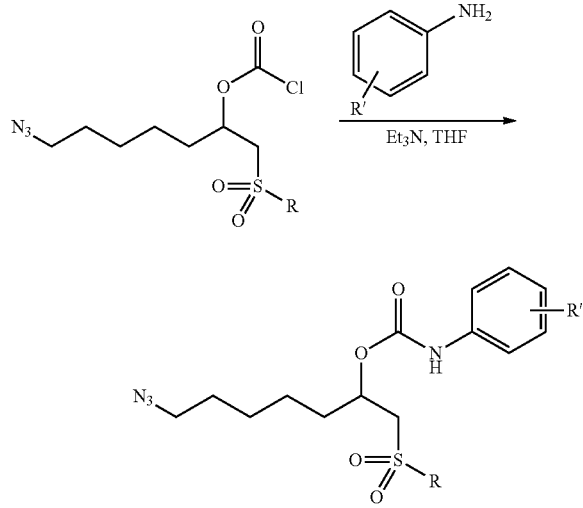

The crude chloroformate prepared from 2.5 mmol of azidoalcohol according to the procedure of Example 5 was dissolved in 20 mL of THF, and the aniline (2.5 mmol) and triethylamine (0.7 mL, 5.0 mmol) were added. After 1 h, the mixture was diluted with ethyl acetate, washed successively with 1N HCl, water, sat. NaHCO$_3$, and brine, then dried over MgSO$_4$, filtered, and evaporated. The residue was chromatographed on silica gel using ethyl acetate/hexane to provide the product carbamate.

Compounds prepared according to this method include:

O-[1-(phenylsulfonyl)-7-azido-2-heptyl]-N-[4-(diethylcarboxamido)phenyl carbamate;

O-[1-(morpholinosulfonyl)-7-azido-2-heptyl]-N-[4-(diethylcarboxamido)phenyl carbamate;

O-[1-(methanesulfonyl)-7-azido-2-heptyl]-N-[4-(diethylcarboxamido)phenyl carbamate;

O-[1-(phenylsulfonyl)-7-azido-2-heptyl]-N-[4-(morpholinocarboxamido)phenyl carbamate; and O-[1-(phenylsulfonyl)-7-azido-2-heptyl]-N-[4-(morpholinosulfonyl)phenyl carbamate.

Example 14

Preparation of N-Chloromethyl Carbamates

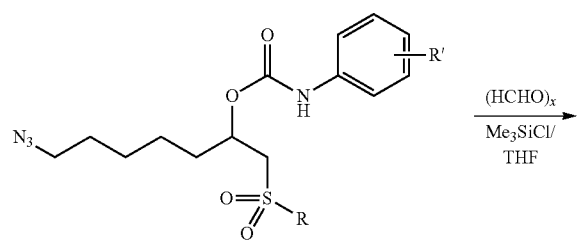

A mixture of the azidocarbamate of Example 13 (1.0 mmol), paraformaldehyde (45 mg), chlorotrimethylsilane (1 mL), and THF (1 mL) in a sealed 20 mL vial was heated in a 55° C. bath for 17 h. After cooling to ambient temperature, the vial was opened and the mixture was concentrated on a rotary evaporator to a thick oil, which was taken up in ethyl acetate and reconcentrated. The residue was dissolved in 2:1 ethyl acetate/hexane, filtered, and concentrated to provide the N-chloromethyl carbamate, which was used without further purification.

Compounds prepared according to this method include:

O-[1-(phenylsulfonyl)-7-azido-2-heptyl]-N-[4-(diethylcarboxamido)phenyl]-N-chloromethyl carbamate;

O-[1-(morpholinosulfonyl)-7-azido-2-heptyl]-N-[4-(diethylcarboxamido)phenyl]-N-chloromethyl carbamate; and O-[1-(methanesulfonyl)-7-azido-2-heptyl]-N-[4-(diethylcarboxamido)phenyl]-N-chloromethyl carbamate.

Example 15

Preparation of N-Alkoxymethyl Carbamates

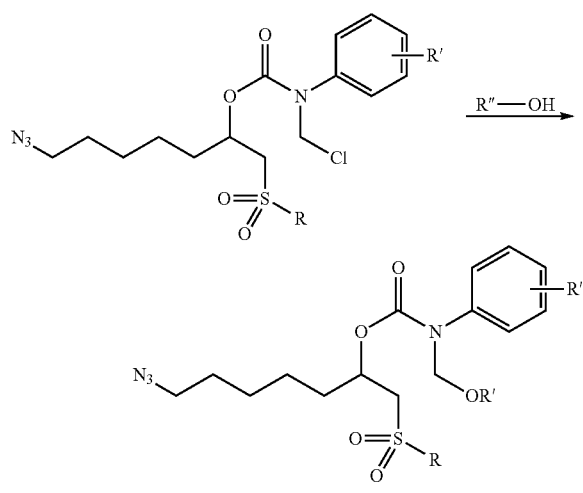

The N-chloromethyl carbamate of Example 14 (0.4 mmol) was dissolved in 5 mL of dry methanol. After 1 h, the mixture is evaporated to dryness, and the residue was chromatographed on silica gel (ethyl acetate/hexanes) to provide the product.

Compounds prepared according to this method include:
O-[1-(phenylsulfonyl)-7-azido-2-heptyl]-N-[4-(diethylcarboxamido)phenyl]-N-methoxymethyl carbamate;
O-[1-(morpholinosulfonyl)-7-azido-2-heptyl]-N-[4-(diethylcarboxamido)phenyl]-N-methoxymethyl carbamate; and
O-[1-(methanesulfonyl)-7-azido-2-heptyl]-N-[4-(diethylcarboxamido)phenyl]-N-methoxymethyl carbamate.

Example 16

7-(Tert-Butoxycarbonylamino)-2-($R^1$-Sulfonyl)-1-Heptanol

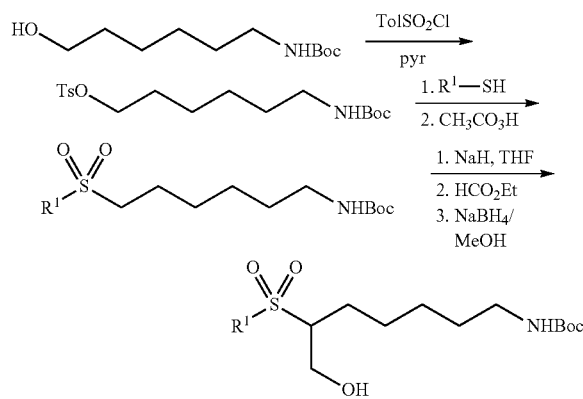

p-Toluenesulfonyl chloride (1 mmol) is added to a solution of 6-azido-1-hexanol (Example 1, 1 mmol) in pyridine (2 mL) cooled on ice. After 30 min, the mixture is allowed to warm to ambient temperature and treated with $R^1$—SH (1 mmol) for an additional 1 hr. The mixture is diluted with ethyl acetate, washed sequentially with water, 1N HCl, water, sat. aq. NaHCO$_3$, and brine, then dried over MgSO$_4$, filtered, and evaporated. The crude thioether is dissolved in ethyl acetate and treated excess peracetic acid to prepare the sulfone. After standard aqueous workup, the sulfone is purified by chromatography on silica gel. A mixture of the sulfone, ethyl formate, and 2 equivalents of sodium hydride in DMF is warmed to 50° C. to provide an intermediate aldehyde, which is treated with sodium borohydride in methanol to produce the product alcohol.

Example 17

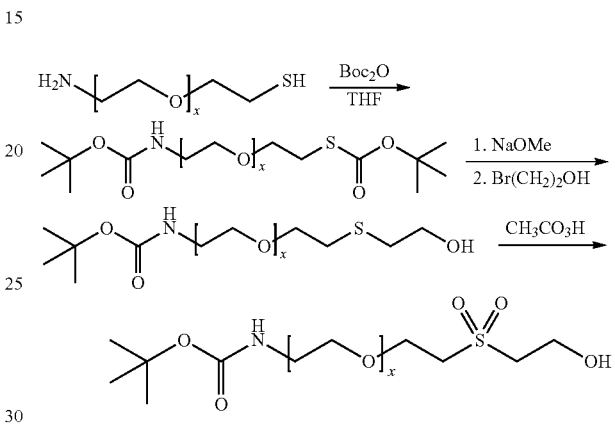

A solution of an amino-thiol heterobifunctional PEG in THF is treated with excess di-tert-butyl dicarbonate until the reaction is complete, and the di-BOC product is isolated by chromatography. The thiocarbonate is cleaved by treatment with one equivalent of NaOMe in methanol, and 2-bromoethanol is added to form the hydroxyethyl thioether, which is oxidized with peracetic acid to form the product.

Example 18

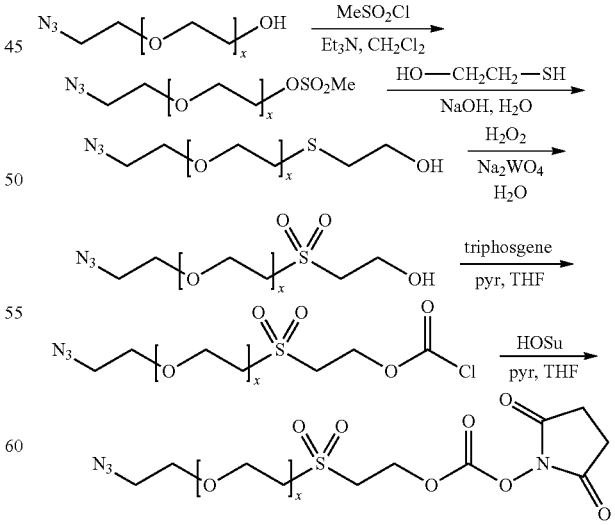

These compounds may be prepared by a method analogous to that described for methoxy-PEG-hydroxyethyl sulfone (Morpurgo, et al., *Bioconjugate Chemistry* (1996)

7:363-368, incorporated herein by reference). For example, a solution of 11-azido-3,6,9-trioxaundecan-1-ol (x=3) (3 mmol) in toluene is dried by azeotropic distillation. After dissolution in $CH_2Cl_2$, methanesulfonyl chloride is added followed by triethylamine to form the mesylate. A solution of the mesylate in water is treated with 2-mercaptoethanol and 2 N NaOH to form the hydroxyethyl sulfide. The sulfide is subsequently oxidized to the sulfone, for example using hydrogen peroxide in the presence of a tungstic acid catalyst or alternatively using peracetic acid. The hydroxyethyl sulfone is then activated as the succinimidyl carbonate according to the methods described in the examples above.

Example 19

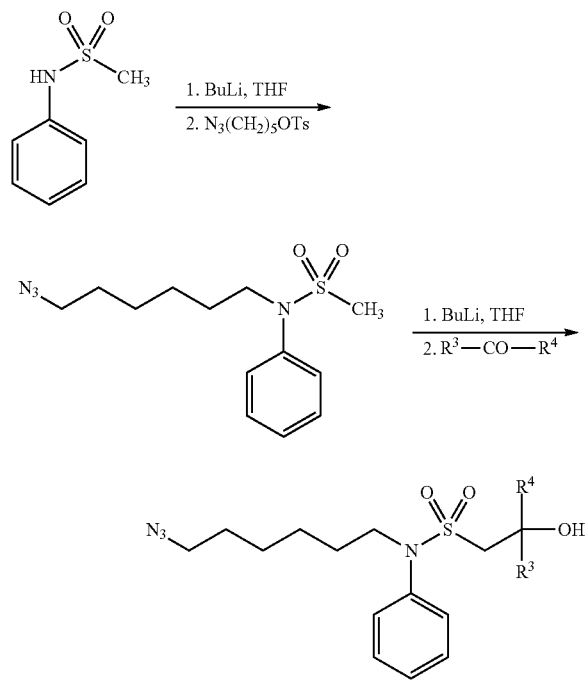

Example 20

Preparation of Crosslinkers of Formula (1)

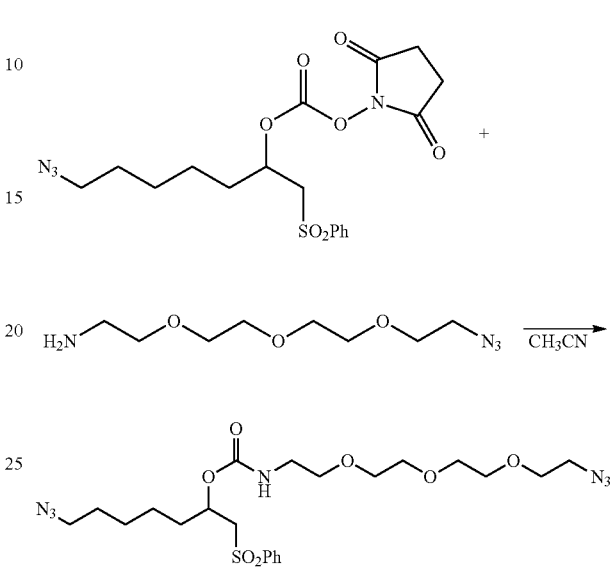

A solution of 7-azido-1-(phenylsulfonyl)-2-hepyl succinimidyl carbonate (119 mg, 0.27 mmol) in 2 mL of acetonitrile was treated with 11-azido-3,6,9-trioxaundecan-1-amine (65 mg, 0.30 mmol) for 10 min at ambient temperature. After evaporation of the solvent, the residue was dissolved in 1 mL of $CH_2Cl_2$ and chromatographed on a 4-g column of silica gel using a step gradient of hexane, 3:1 hexane/ethyl acetate, 1:1 hexane/ethyl acetate, and 1:2 hexane/ethyl acetate. The product-containing fractions were pooled and evaporated to provide the product.

Example 21

Preparation of 4-arm PEG-[DBCO]$_4$

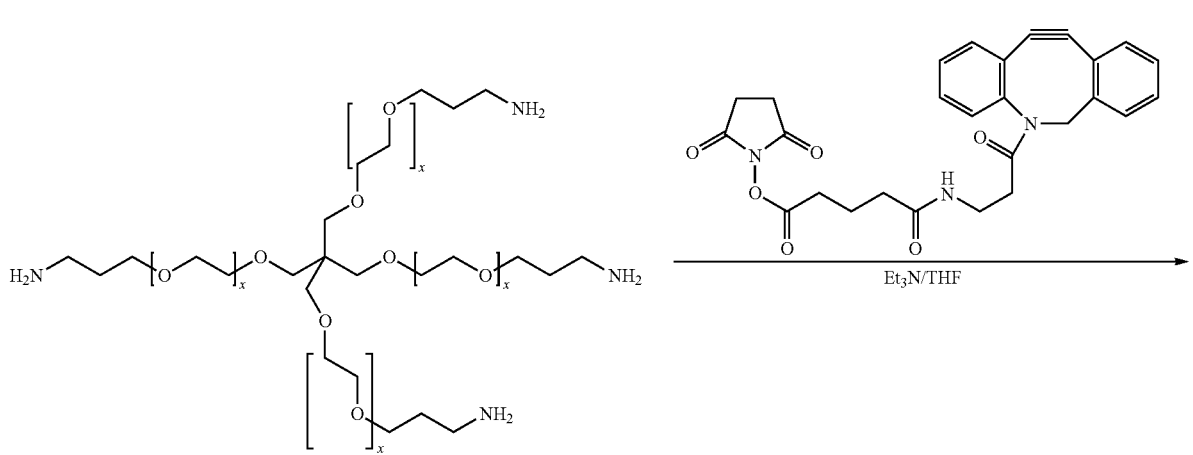

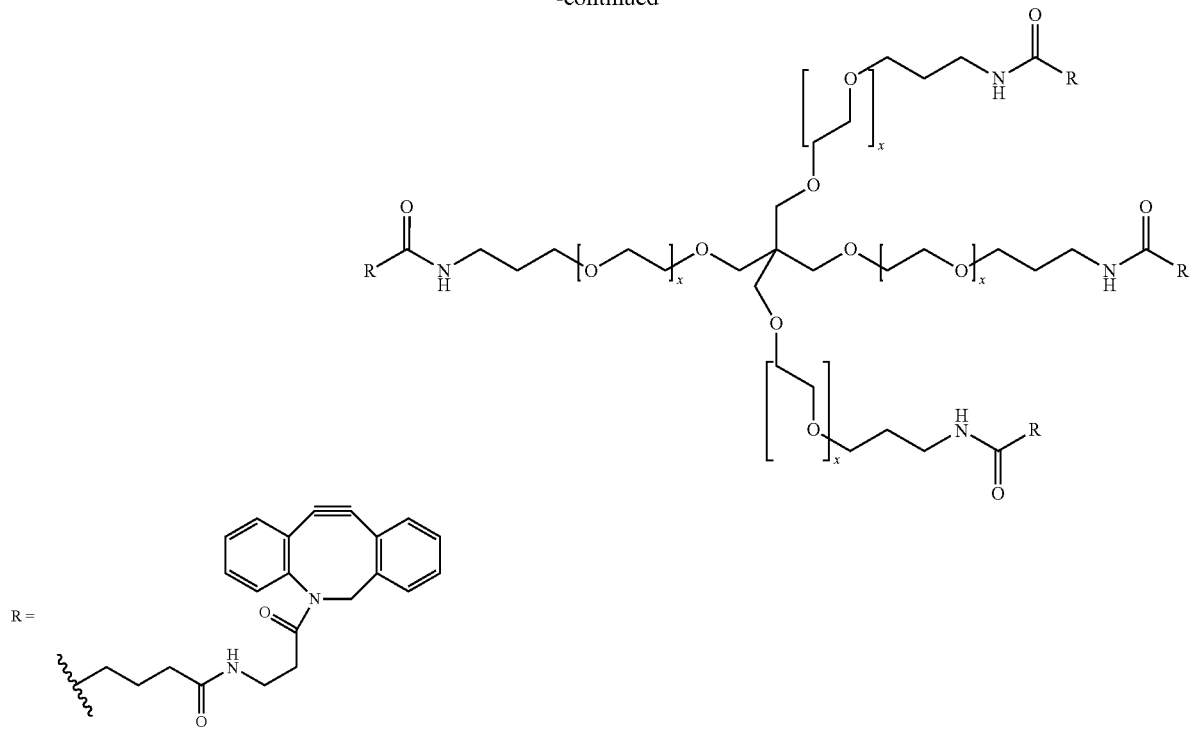

A solution of 40-kDa 4-arm polyethylene glycol with aminopropyl end-groups having a pentaerythritol core (NOF America, PTE400PA) (500 mg, 12.5 μmol), triethylamine (20 μL), and 6-aza-5,9-dioxo-9-(1,2-didehydrodibenzo[b,f] azocin-5(6H)-yl)nonanoic acid succinimidyl ester ("DBCO-NHS", Click Chemistry Tools, Macon, Ga.) (36 mg, 75 μmol) in 5 mL of THF was stirred for 24 h at ambient temperature. The product was precipitated by addition of the reaction mixture to 50 mL of methyl tert-butyl ether (MTBE). The precipitate was collected by vacuum filtration and dried under vacuum to provide 510 mg of product.

Example 22

Hydrogel Formation

A solution of 4.5 mg of 4-arm PEG-[DBCO]$_4$ (Example 21) in 100 μL of 10 mM acetate buffer, pH 5, was treated with 5.0 μL of a 40 mg/mL solution of the diazide crosslinker of Example 20. The solution rapidly set to provide an elastic hydrogel.

Similarly, a solution of 4.5 mg of 4-arm PEG-[DBCO]$_4$ (Example 21) in 100 μL of 10 mM acetate buffer, pH 5, was treated with 2.5 μL of a 40 mg/mL solution of the diazide crosslinker of Example 20. The solution gelled to produce a viscous hydrogel.

Example 23

Preparation of Multivalent PEG-(Linker-Azide)$_x$ Crosslinking Reagents of Formula (2)

The preparation of multivalent PEG-(linker-azide)$_x$ crosslinking reagents is exemplified by the preparation of a compound of formula (2) wherein m=0, n=approximately 100, s=0, t=4, W=O(C=O)NH, Q=C(CH$_2$)$_4$, R$^1$=PhSO$_2$, R$^2$=H, one R$^5$=H and the other R$^5$=(CH$_2$)$_5$N$_3$. Other compounds of formula (2) were prepared using the same method by substitution of the appropriate azide-linker-succinimidyl carbonate of Example 7. As necessary, analogous azide-linker-succinimidyl carbonates of other Examples may also be used.

Thus, a solution of 25 μmol of the azido-linker-succinimidyl carbonate (Example 7) in 1 mL of ACN was added to a mix of 5 μmol (100 mg) of 20-kDa 4-arm PEG-amine hydrochloride (pentaerythritol core, JenKem Technologies) in 1 mL of water and 40 μL of 1.0 M NaHCO$_3$ (40 μmol). After 1 hr at ambient temperature the solution was dialyzed (12-14 k MWCO) against 1 L of 50% methanol followed by 1 L of methanol. After evaporation, the residue (109 mg) was dissolved in 2.12 mL of sterile-filtered 10 mM NaOAc, pH 5.0, and stored frozen at −20° C. The azide concentration determined by reaction with DBCO-acid was 9.5 mM.

Example 24

Preparation of Multivalent PEG-(Cyclooctynes)$_x$

PEG$_{20kDa}$-(DBCO)$_4$: A 60 mM solution of freshly chromatographed DBCO—NHS (Click Chemistry Tools) in acetonitrile (0.5 mL, 30 μmol, 1.5 eq) was added to a solution of 20 kDa 4-arm PEG-amine hydrochloride (pentaerythritol core, JenKem Technologies; 100 mg, 5 μmol), and diisopropylethylamine (0.010 mL, 57 μmol) in acetonitrile (1 mL). After stirring 2 h at ambient temperature, the mixture was evaporated to dryness under reduced pressure. The residue was dissolved in 50% aqueous methanol (4 mL) and dialyzed against 50% aqueous methanol followed by methanol. After evaporation, the residue (100 mg) was dissolved in water to give a 50 mg/mL stock (10 mM DBCO by spectrophotometric assay), which was stored frozen at −20° C.

PEG$_{40kDa}$-(DBCO)$_8$: One mL of 40 mM solution (40 μmol) of DBCO—NHS in THF was added to a solution of 168 mg (4.2 μmol) of 40-kDa 8-arm PEG-amine hydrochloride (tripentaerythritol core, JenKem Technologies) and 12.9 μL diisopropylethylamine (74 μmol) in 0.6 mL of ACN, and the mixture was kept at ambient temperature overnight. The reaction mixture was dialyzed against 2 L of 50% methanol followed by 1 L of methanol. After evaporation, the residue (149 mg) was dissolved in 1.49 mL water and stored frozen at −20° C. The DBCO concentration determined spectrophotometrically was 16 mM.

PEG$_{40kDa}$(BCN)$_8$: A solution of 200 mg of 40 kDa 8-arm PEG-amine.HCl (JenKem Technologies; 40 μmol NH$_2$), 20 mg of BCN p-nitrophenyl carbonate (SynAffix; 63 μmol), and 20 μL of N,N-diisopropylethylamine (115 μmol) in 2 mL of DMF was stirred 16 h at ambient temperature. After quenching with 0.5 mL of 100 mM taurine in 0.1M KP$_i$, pH 7.5, for 1 h, the mixture was dialyzed sequentially against water, 1:1 methanol/water, and methanol using a 12 kDa membrane. After evaporation, the residue was dissolved in 2 mL of THF and precipitated with 10 mL of methyl $^t$butyl ether. The product was collected and dried (190 mg).

Example 25

Preparation of BODIPY-Azide Erosion Probe

A 100 mM solution of 11-azido-3,6,9-trioxaundecan-1-amine in acetonitrile (13 μL, 13 μmol) was added to a 12.8 mM solution of BODIPY TMR-X SE (Invitrogen) in DMSO (100 μL, 1.28 mol). After 30 min at ambient temperature, the mixture was diluted to 2 mL with 0.1M KP$_i$, pH 7.4, and loaded on a 500 mg C18 BondElut™ extraction column (Varian). The column was washed successively with 5 mL portions of water and 20% ACN/water, then eluted with 50% ACN/water and concentrated to dryness. The residue was dissolved in 1.0 mL of ACN and the concentration (1.0 mM) was determined using $\epsilon_{544}$ nm=60,000 M$^{-1}$ cm$^{-1}$.

Example 26

Preparation of Fluorescein-Azide Erosion Probe

A 10 mg/mL solution of 5-(aminoacetamido)fluorescein (Invitrogen) in DMF (100 μL) was mixed with a 25 mM solution of 6-azidohexyloxy succinimidyl carbonate (100 μL) for 1 h to provide a 12.5 mM solution of the fluorescein-azide erosion probe.

Example 27

Preparation of Hydrogels Using Multivalent Crosslinking Reagents of Formula (2)

For preparation of 4×4 hydrogels, a 50 mg/mL solution of PEG$_{20kDa}$(DBCO)$_4$ (Example 24; 250 μL, 2.5 μmol DBCO end-groups) in water was mixed with 25 μL of a 10 mM solution of the fluorescein-azide erosion probe in DMF (Example 26; 0.25 μmol azide) and kept 30 min at ambient temperature. Fifty μL aliquots (0.42 μmol DBCO) were mixed with 28 μL of 10 mM NaOAc, pH 5.0, followed by 42 μL of 50 mg/mL PEG$_{20kDa}$(linker-azide)$_4$ (Example 23; 0.42 μmol azide). Components were mixed by vortexing, centrifuged briefly to remove any air bubbles, and quickly pipetted into 64 μL (9×1 mm) circular rubber perfusion chambers (Grace Bio-Labs) mounted on a silanized glass microscope slide, and allowed to cure overnight.

Preparation of 4×8 hydrogels followed the same method, using solutions of PEG$_{40kDa}$(DBCO)$_8$ or PEG$_{40kDa}$(BCN)$_8$ (Example 24) in place of PEG$_{20kDa}$(DBCO)$_4$ and adjusting the proportions of 8-armed cyclooctyne and 4-armed linker-azide monomers so as to provide gels having the desired total wt % PEG and degree of crosslinking.

Example 28

Measurement of Reverse Gelation Times

Figure 5:
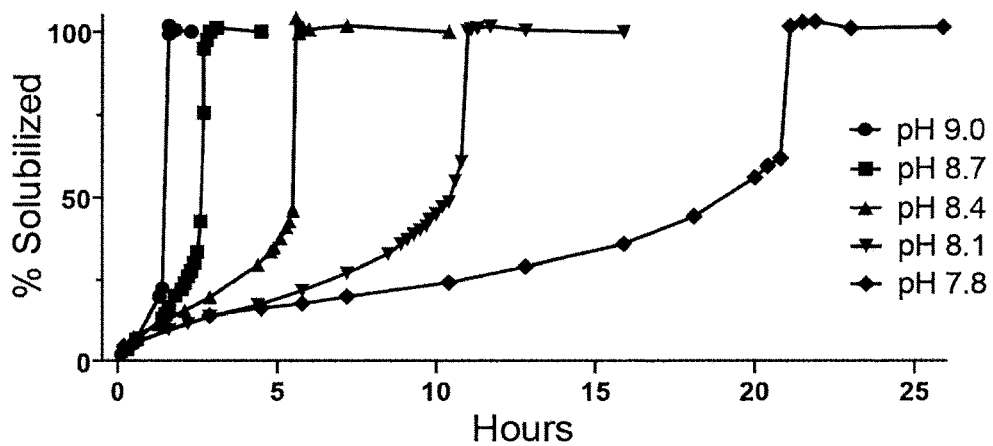
FIG. 5 shows the pH dependence for degelation of 4×4 PEG hydrogels of Example 28, wherein $L_2$ has modulator $R^1$=(4-chlorophenyl)$SO_2$.
Figure 6:
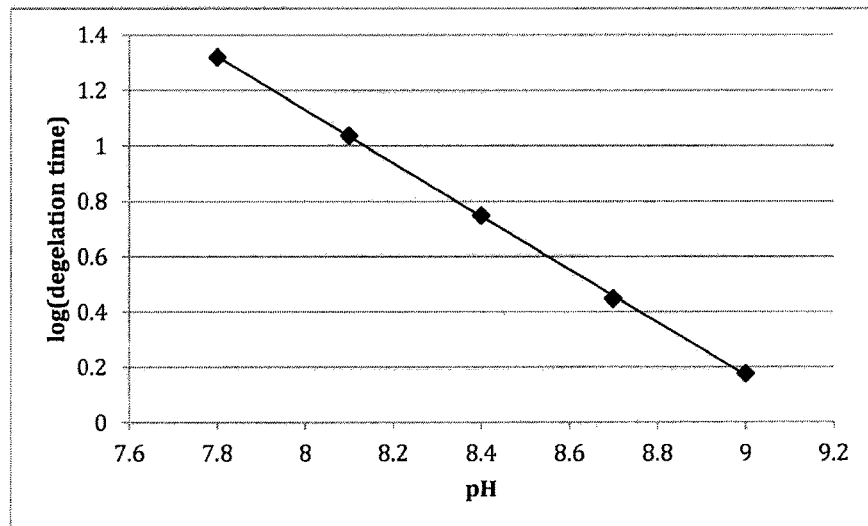
FIG. 6 shows the correlation between pH and degelation time for the gels of Example 28.

Gel discs (Example 27) were suspended in buffer at 37° C., and OD$_{493}$ in the solution was periodically measured to monitor fluorescein solubilization. The reverse gelation times (t$_{RGEL}$) were those times when gels were completely solubilized. The pH dependence of the degelation time was determined using 4×4 gels (5% total PEG by weight) prepared from PEG$_{20kDa}$(DBCO)$_4$ crosslinked using a compound of formula (2) wherein m=0, n=approximately 100, s=0, t=4, W=O(C=O)NH, Q=C(CH$_2$)$_4$, R$^1$=(4-chlorophenyl)SO$_2$, R$^2$=H, one R$^5$=H and the other R$^5$=(CH$_2$)$_5$N$_3$. The gel discs were suspended in buffers from pH 7.8-9.0. Degelation curves are shown in FIG. 5, with measured times at pH 7.8=20.9 h, pH 8.1=10.9 h, pH 8.4=5.6 h, pH 8.7=2.8 h, and pH 9.0=1.5 h. As shown in FIG. 6, the degelation time varies linearly with pH, increasing 10-fold for each drop of 1 pH unit.

Figure 4:
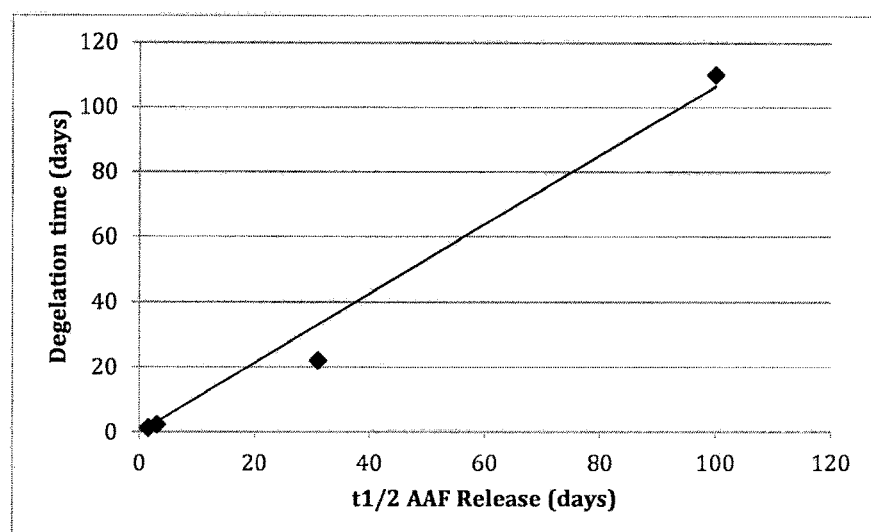
FIG. 4 shows the correlation between the degelation times measured for 4×4 hydrogels of Example 28 and the rate of 5-(aminoacetamido)fluorescein release measured from soluble PEG conjugates using equivalent linkers.

The effect of the linker modulator R$^1$ on degelation time was determined by preparing hydrogel discs from PEG$_{20kDa}$(DBCO)$_4$ crosslinked using compounds of formula (2) wherein m=0, n=approximately 100, s=0, t=4, W=O(C=O)NH, Q=C(CH$_2$)$_4$, R$^2$=H, one R$^5$=H and the other R$^5$=(CH$_2$)$_5$N$_3$, and wherein R$^1$ was either (4-chlorophenyl)SO$_2$, phenyl-SO$_2$, morpholino-SO$_2$, or CN. A control gel was prepared having no modulator (R$^1$R$^2$CH is absent). Degelation curves of the discs suspended in KP$_i$, pH 7.4, 37° C., are shown in FIG. 3. As shown in FIG. 4, there is a linear correlation between the half-life of linker cleavage as determined by release of 5-(aminoacetamido)fluorescein (see Santi, et al., *Proc. Nat. Acad. Sci. USA* (2012) 109:6211-6216), incorporated herein by reference, and the degelation time of the corresponding hydrogel.

Example 29

Controlled Drug Release from Hydrogels

Hydrogels were prepared from PEG$_{40kDa}$-(DBCO)$_8$ wherein a fraction of the cyclooctynes were first reacted with a small amount of azide erosion probe and with an azide-linker-drug of formula (3) wherein the linker comprised a modulating group R$^1$, then crosslinked using a compound of formula (2) wherein m=0, n=approximately 100, s=0, t=4, W=O(C=O)NH, Q=C(CH$_2$)$_4$, R$^2$=H, one R$^5$=H and the other R$^5$=(CH$_2$)$_5$N$_3$, and wherein R$^1$ was either (4-chlorophenyl)SO$_2$, phenyl-SO$_2$, morpholino-SO$_2$, or CN. The modulating groups of the azide-linker-drug of Formula (3) and the compound of formula (2) were chosen such that release of drug would occur more rapidly than erosion and subsequent degelation of the hydrogel.

In one example, gels were prepared using 5-(acetamido) fluorescein (AAF) as a drug surrogate. The modulating R$^1$ groups in Formula (3) were varied as noted below. Thus a solution (99.6 μL) containing 50 μL of 100 mg/mL PEG$_{40kDa}$-(DBCO)$_8$ (1.0 μmol DBCO end groups) in water was mixed with 6.2 μL of 12.5 mM of azide-linker-AAF (0.078 μmol) in 1:1 DMF:acetonitrile (where the linker comprised one of various modulators), 15 μL of 1.0 mM BODIPY-azide (0.015 μmol) in acetonitrile as an erosion probe, 20 μL of 20 mM O-(2-azidoethyl)heptaethylene glycol (0.40 μmol) in water to cap excess cyclooctynes, and 8.4 μL water. After 10 min at ambient temperature, the solution containing 0.5 μmol uncommitted DBCO groups was mixed with 50 μL of a 50 mg/mL solution of the compound of formula (2) wherein $R^1$=$CH_3$—$SO_2$ (0.5 μmol azide groups) in 10 mM NaOAc, pH 5.0.

Figure 7:
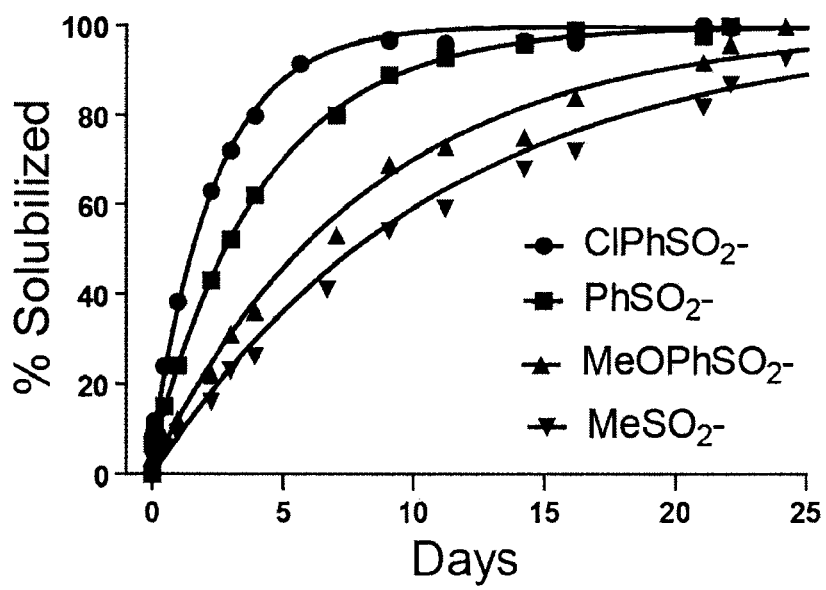
FIG. 7 shows the release of drug surrogate 5-(aminoacetamido)fluorescein from 4×8 PEG hydrogels of Example 29.

Duplicate cast gels were suspended in 0.1M HEPES, pH 7.4, at 37° C., and $OD_{493}$ for fluorescein and $OD_{546}$ for BODIPY in the solution was periodically measured. The release times for fluorescein where $R^1$ in Formula 3 is of various groups was measured as shown in FIG. 7. The reverse gelation time, as determined by complete solubilization of the BODIPY erosion probe, was 630±39 (S.D.) hr (n=8). Solubilization of fluorescein followed the first-order rate law $[F]_t/F_{tot}=\exp(-k_{obsd}t)$ and gave apparent $k_{obsd}$±S.E. for the total released fluorescein of 0.021±0.00014 hr$^{-1}$ for $R^1$=4-ClPh-$SO_2$—, 0.011±0.00031 hr$^{-1}$ for $R^1$=Ph-$SO_2$—, 0.0053±0.00022 hr$^{-4}$ for $R^1$=4-MeO-Ph-$SO_2$—, and 0.0033±0.00010 hr$^{-1}$ for $R^1$=MeSO$_2$—. The rate data were converted to plots for the fluorescein released directly from the gel using Eq. S6 (Example 30).

Figure 8:
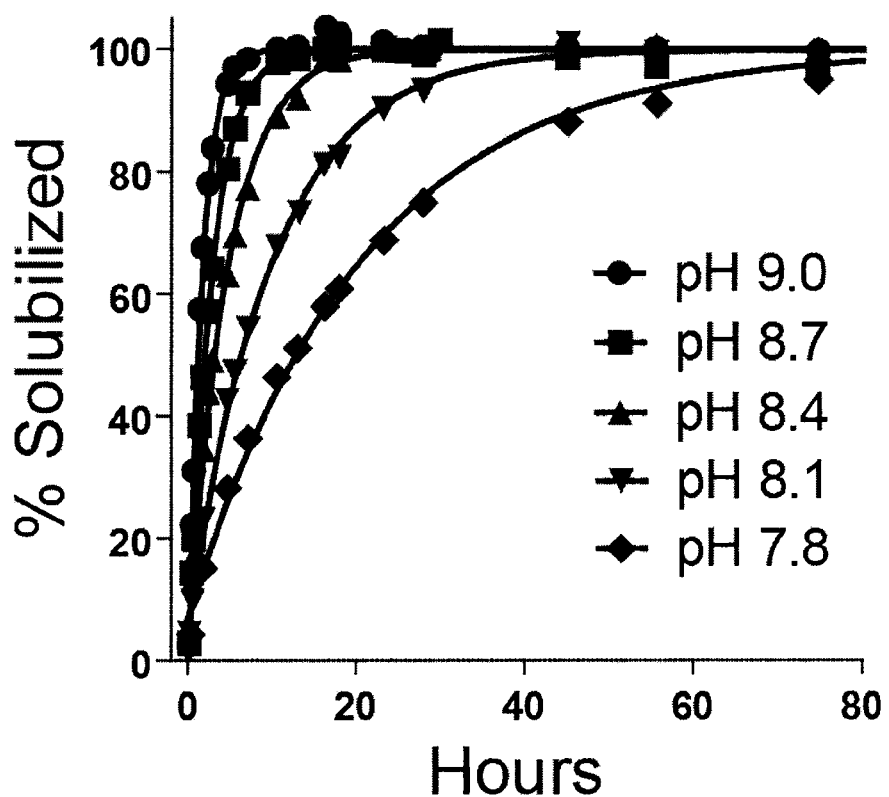
FIG. 8 shows the pH dependence of the release of drug surrogate 5-(aminoacetamido)fluorescein from 4×8 PEG hydrogels of Example 29. The half-lives for release were measured at pH 7.4 (23.0 h); pH 7.8 (14.0 h); pH 8.1 (6.9 h); pH 8.4 (3.2 h); pH 8.7 (1.9 h); and pH 9.0 (1.1 h).
Figure 9:
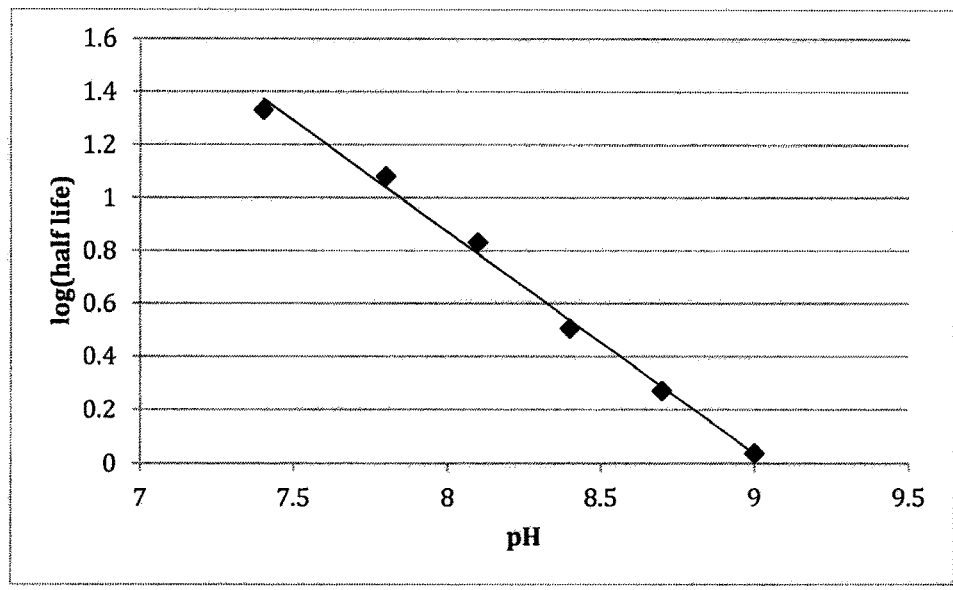
FIG. 9 shows the correlation between the pH and the half-lives for drug release from the 8×4 hydrogels of Example 29.

The pH-dependence of drug release was determined by observing AAF release from the above gels prepared using $R^1$=(4-chlorophenyl)$SO_2$ between pH 7.4 and 9.0. As shown in FIGS. 8 and 9, the rate of drug release increases with increasing pH.

Example 30

Modeling of Drug Release and Gel Erosion

Drug release and gel degradation occurs as follows, with the final products being the free drug and gel monomers:

(Gel)–(Drug)$_n$→Drug+EP-gel fragment–Drug→Drug+EP-monomers

The drug or drug surrogate released into solution may emanate directly from L1 cleavage from the gel, or from solubilized fragments that arise from gel erosion via cleavages of L2. To distinguish the drug released from the intact gel vs. solubilized gel fragments, it is necessary to determine the distribution of drug-bearing nodes between the intact gel and solution at time t. In the present study, we used a modification of a reported approach to monitor and model gel degradation (2). The appearance of an erosion probe EP permanently attached to nodes of the gel allows calculation of the fraction of nodes in solution as $EP(t)/E_\infty$; the concentration of drug originally present on these solubilized nodes, $D_s(t)$, is thus given by Eq. S1.

$$D_s(t)=D_\infty * EP(t)/EP_\infty \text{ or } (D_\infty/EP_\infty)*EP(t) \quad [S1]$$

The drug released from the intact gel at time t, $D_g(t)$, is the difference between the total drug released, $D(t)$, and the drug either contained in or released from solubilized gel fragments $D_s(t)$, as in Eq. S2.

$$D_g(t)=D(t)-D_s(t)=D(t)-(D_\infty/EP_\infty)*EP(t) \quad [S2]$$

Calculation of the first-order rate of drug release from intact gel nodes is not straightforward from measuring D(t) due to the changing quantity of gel from erosion, but can be calculated based on the fraction of drug remaining on intact gel. Based on released erosion probe EP(t), the fraction of gel remaining is 1−$EP(t)/EP_\infty$). The amount of drug originally carried by this amount of gel is thus given by $D_\infty*(1-EP(t)/EP_\infty)$. As the drug remaining on the intact gel is $D_\infty - D(t)$, the fraction of drug remaining on intact gel, $D_{f,gel}(t)$ is given as Eqs. S3-S4.

$$D_{f,gel}(t) = [D_\infty - D(t)]/[D_\infty *(1 - EP(t)/EP_\infty)] \quad [S3]$$

$$= [1 - D(t)/D_\infty]/[1 - EP(t)/EP_\infty] \quad [S4]$$

For a first order release of drug from the gel, $D_{f,gel}(t)$ will show an exponential decay having a rate constant $k_{L1}$ that describes the rate of drug release from intact gel, Eq. S5. Merging Eq. S4 and S5 provides S6 which can be used to experimentally estimate the rate of drug release directly from intact gel.

$$D_{f,gel}(t)=e^{-k_{L1}t} \quad [S5]$$

$$D_{f,gel}(t)=[1-D(t)/D_\infty]/[1-EP(t)/EP_\infty]=e^{-k_{L1}t} \quad [S6]$$

The amount of drug released by the gel over time depends on the rate of release, $k_{L1}$, together with the erosion rate of the gel. If the solubilization of the erosion probe can be approximated by a first order process between times t=0 and $t_1$ with rate $k_{sol}$, the quantity of drug released from the gel during that time can be approximated as Eq. S7.

$$D_g(t_1)=D_\infty*(k_{L1}/(k_{sol}))*[1-e^{-(k_{sol})t_1}] \quad [S7]$$

If the drug remaining on the intact gel is negligible at time $t_1$, then the total fraction of drug directly released from the gel is given in Eq. S8

$$D_g(t_1)/D_\infty=k_{L1}/k_{sol}=t_{1/2,sol}/t_{1/2,L1} \quad [S8].$$

Example 31

Effect of Crosslink Density on Degelation Time

As detailed in Table 1, a mixture of 100 mg/mL $PEG_{40kDa}$-(BCN)$_8$ (20 mM BCN end-groups) in water was combined with appropriate amounts of 10 mM fluorescein-azide and the compound of Formula (2) wherein m=0, n=approximately 100, s=0, t=4, W=O(C=O)NH, Q=C(CH$_2$)$_4$, $R^2$=H, one $R^5$=H and the other $R^5$=(CH$_2$)$_5$N$_3$, and $R^1$=(4-chlorophenyl)SO$_2$ (10 mM azide) in water and 50 mM O-azidoethyl-heptaethylene glycol in water to prepare 4% PEG hydrogels having 4, 5, 6, 7, or 7.8 crosslinks per 8-arm PEG monomer. Cast gels were placed in 1 mL of 0.1M borate, pH 9.2, and kept at 37° C. Dissolution of the gels was monitored by appearance of $OD_{493}$ in the supernatant.

TABLE 1

Preparation and degelation times of gels with varying crosslinking densities.

| | Crosslinks/8-arm PEG | | | | |
|---|---|---|---|---|---|
| | 4 | 5 | 6 | 7 | 7.8 |
| PEG-(BCN)$_8$ | 40 μL | 36.9 μL | 34.3 μL | 32.0 μL | 30.4 μL |
| Fluorescein-azide | 1.5 μL | 1.5 μL | 1.5 μL | 1.5 μL | 1.5 μL |
| Cap-azide | 7.7 μL | 5.2 μL | 3.1 μL | 1.3 μL | 0 μL |
| PEG-(L2-N$_3$)$_4$ | 40 μL | 46.2 μL | 51.4 μL | 56.0 μL | 59.2 μL |
| Water | 60.8 μL | 60.2 μL | 59.7 μL | 59.2 μL | 58.9 μL |
| Degelation time (pH 9.2) | 0.62 h | 0.77 h | 0.83 h | 0.88 h | 0.97 h |

TABLE 1-continued

Preparation and degelation times of gels with varying crosslinking densities.

| | Crosslinks/8-arm PEG | | | | |
|---|---|---|---|---|---|
| | 4 | 5 | 6 | 7 | 7.8 |
| Degelation time (pH 7.4) | 37 h | 46 h | 50 h | 53 h | 58 h |

Gels dissolved at pH 9.2 with degelation times as indicated in Table 1, with the degelation time at pH 7.4 calculated as (degelation time at pH 9.2)*$10^{(9.2-7.4)}$ as determined in Example 28. As expected, degelation time increased with increasing number of crosslinks to each 8-arm monomer.

Example 32

Preparation of an Exenatide-Releasing Degradable Hydrogel

Exenatide linked at the α-terminus to an azide-linker having $R^1$=MeSO$_2$— as modulator was synthesized by solid-phase peptide synthesis at AnaSpec (Fremont, Calif.) as previously described (Santi, et al., *Proc. Nat. Acad. Sci. USA* (2012) 109:6211-6216), resulting in a compounds of formula (3) wherein $R^1$=MeSO$_2$, $R^2$=H, m=0, one $R^5$=H and the other $R^5$=(CH$_2$)$_5$N$_3$, Y=NH, and D=exenatide linked via the N-terminal amino group. Azide-linker-exenatide (1.2 mg, 270 nmol) in 30 μL of 1.0 M phosphate, pH 7.8, and 8-arm PEG$_{40kD}$-(BCN)$_8$ (Example 24; 5 mg; 50 μL, 1000 nmol BCN groups) in 50 μL of water was kept for 1 hr at ambient temperature, then 20 μL of a 1 mM BODIPY-azide (20 nmol) in ACN as erosion probe and a crosslinker of formula (2) wherein m=0, n=approximately 100, s=0, t=4, W=O(C=O)NH, Q=C(CH$_2$)$_4$, $R^2$=H, one $R^5$=H and the other $R^5$=(CH$_2$)$_5$N$_3$, and $R^1$=CN (3.55 mg; 710 nmol N$_3$ groups; Example 23) in 71 water was added. The gels were allowed to cure overnight, then stored in 1 mL of PBS, pH 7.4, at 4° C.

Example 33

Release of Exenatide from an Exenatide-Releasing Degradable Hydrogel

Figure 10:
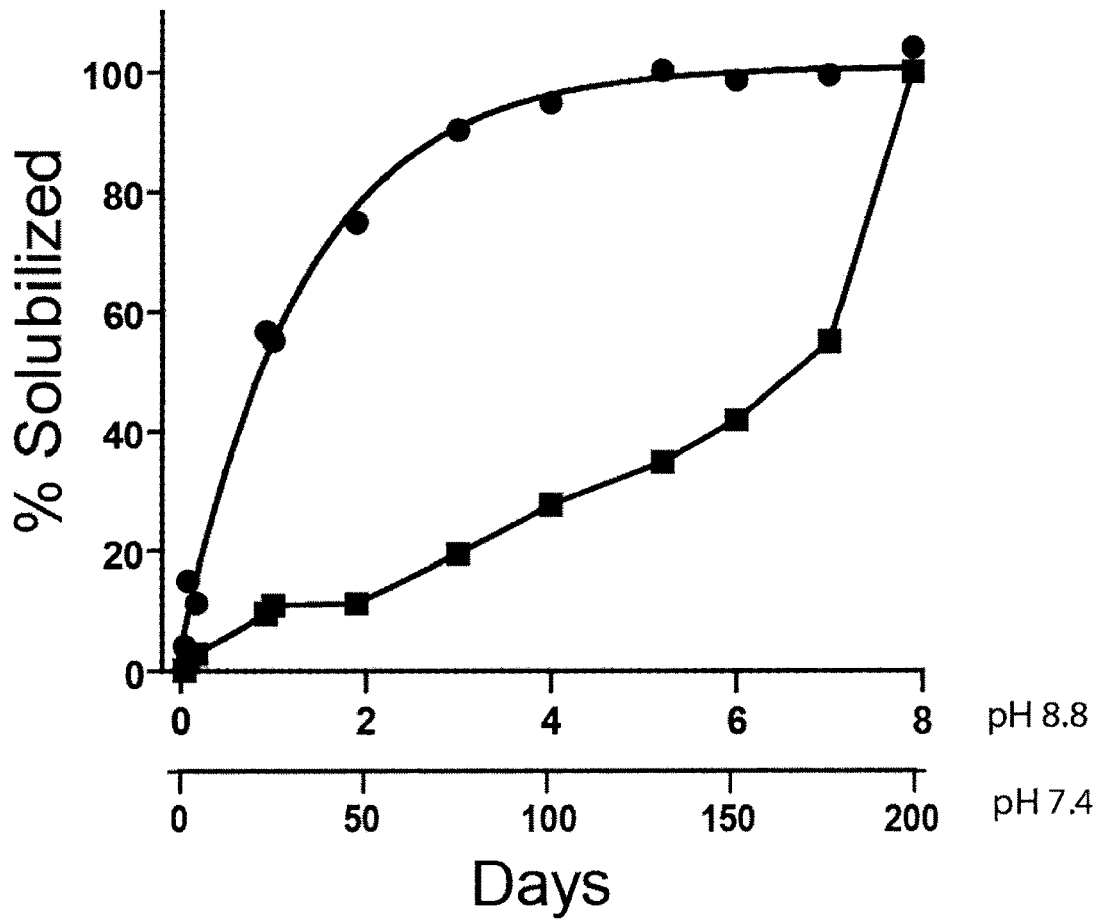
FIG. 10 shows the release of the peptide exenatide (exendin-4) covalently attached via a releasable linker $L_1$ having modulator $R^{11}$=$CH_3SO_2$ to an 8×4 PEG hydrogel crosslinked with degradable linkers $L_2$ having modulator $R^1$=CN at pH 8.8, 37° C. (Example 33). Knowing the pH-dependence of linker release and gel degradation, the corresponding scale at pH 7.4 is also given. Total solubilized exenatide (circles) is released with apparent $t_{1/2}$=20.7 h at pH 8.8, corresponding to $t_{1/2}$=21 days at pH 7.4. Degelation (squares=solubilized fluorescein erosion probe) was observed at 172 h at pH 8.8, corresponding to 180 days at pH 7.4.

A gel disc (Example 32) was placed in 1.0 mL of 0.1M borate buffer, pH 8.8, and kept at 37° C. Solubilization of exenatide (either as free peptide or as solubilized gel-exenatide fragments) and gel erosion were monitored at 280 nm and 544 nm, respectively, by periodic sampling of the supernatant. These results are shown in FIG. 10. Release was calculated as solubilization adjusted for gel erosion. Exenatide solubilization was a first-order process with $t_{1/2}$=20.7 h at pH 8.8 which, assuming the reaction is first order in hydroxide ion, corresponds to a half-life of 520 h (21 days) at pH 7.4; a $t_{1/2}$ of 23.6 h at pH 8.8, corresponding to 593 h (24.7 d) at pH 7.4 was calculated for the drug directly released from the gel (Example 30), which accounted for ~87.8% of the total exenatide. Reverse gelation was observed at 172 h at pH 8.8, corresponding to approximately 180 days at pH 7.4.

Example 34

Diffusion of Encapsulated Proteins from Hydrogels

Stock solutions of ~90 OD$_{280}$/mL myoglobin (17.7 kDa), carbonic anhydrase (29.0 kDa), and BSA (66.4 kDa) were prepared in 0.1M KP$_i$, pH 7.4. PEG hydrogels (4%) were prepared by adding 100 mg/mL PEG$_{20kDa}$-(NHCO$_2$(CH2)$_6$N$_3$)$_4$ (50 uL) to a mixture of 100 mg/mL 20 kDa PEG-(DBCO)$_4$ (50 μL), protein stock (50 μL), and 10×-PBS (100 μL). Cast gels were suspended in 2 mL of 0.1M KP$_i$, pH 7.4, at 37° C., and OD$_{280}$ in the solution was periodically measured. The $t_{1/2}$ values for release into solution were ~20 min for myoglobin 24 min for carbonic anhydrase and 150 min for BSA.

Example 35

Preparation of Derivatized Hyaluronic Acids

Sodium Hyaluronate of mw=1.6×10$^6$ (Lifecore Biomedical; 10.4 mg, 0.0275 mmol carboxylate) was treated with a solution of 4-(4,6-dimethoxy-1,3,5-triazin-2-yl)-4-methyl-morpholinium chloride (DMTMM; 30.4 mg, 0.110 mmol, 4 equiv) in 1.05 mL of 0.1M MES buffer, pH 5.5. The resulting mixture was shaken vigorously for 15 min to dissolve. A solution of DBCO-PEG4-NH2 (Click Chemistry Tools; 0.113 mL of 24.3 mM in 2:1 ACN:MeOH, 0.00275 mmol, 0.1 equiv) in 0.3 mL of MES buffer was added. The resulting mixture was allowed to stand for 24 h then analyzed for the consumption of free amine by TNBS assay at 3.5 and 24 h as follows: 0.05 mL of the reaction mixture was diluted to 1 ml in 0.075 M borate buffer (pH 9.34) containing 0.004% w/v 2,4,6-trinitrobenzesulfonic acid and 25% methanol. The absorbance of the reaction at 420 nm was followed until stable (~1 h). Reactions containing amounts of DMTMM, hyaluronic acid, or DBCO-PEG4-NH2 were used as controls. Upon completion, the reaction mixture was diluted with 8 mL of water and dialyzed (12000-14000 MWCO) five times against water then once against methanol. The dialyzed product was concentrated to dryness under reduced pressure and desiccated under hard vacuum over P$_2$O$_5$ to give DBCO-hyaluronic acid (11 mg, ~0.029 mmol disaccharide) as a clear dry glassy solid. This material was dissolved in 3 mL of water to give slightly greasy very viscous solution containing 0.276 mM DBCO (based on $\epsilon_{309}$=13,448 M$^{-1}$ cm$^{-1}$. This corresponds to a degree of substitution of 2.9% (5.3% based on amine consumed in TNBS assay). Hyaluronic acids of different molecular weights may be derivatized with cyclooctyne reagents, such as DIFO or BCN, according to this method.

Amine-derivatized hyaluronic acids were prepared according to the following method. To a solution of sodium hyaluronate of MW=76,000 (Lifecore Biomedical; 154 mg, 0.385 mmol disaccharide/carboxylate) in water (4 mL) was added 1,3-diaminopropane (0.973 mL, 856 mg, 11.6 mmol, 30 equiv). The pH of the resulting solution was adjusted to 7.0 with 6 N HCl (final volume ~7 mL) then solid N-hydroxysuccinimide was added (177 mg, 1.54 mmol, 4 equiv), followed by solid 1-(3-dimethylamino)propyl-3-ethylcarbodiimide HCl salt (294 mg, 1.54 mmol, 4 equiv). The reaction became acidic as it progressed (pH 5.3 after 10 min). Every 10 min the pH was adjusted back to 7.2 until stable (~1 h). After stirring for 18 h the mixture was dialyzed (12-14 k MWCO) against PBS, 5% NaCl, twice against water, then against methanol. The mixture was concentrated to dryness to give 85 mg of propylamino-hyaluronic acid as a white solid. An aliquot of this material (7.4 mg, ~0.019 mmol disaccharide) was dissolved in water (0.5 mL) to give a solution of ~38 mM disaccharide. This solution (0.025 mL) was assessed for free amine content by TNBS assay by incubating in pH 9.36 borate buffer (1 mL) containing 0.02% w/v TNBS. The absorbance at 420 nm was monitored until stable (~1 h). The assay indicated a degree of substitution of 7%.

To a solution of mw=$1.6 \times 10^6$ 7% DS propylamino HA (0.5 mL of 0.64 mM $NH_2$, 320 nmol $NH_2$) in water was added 0.1 mL of 100 mM PBS, followed by a solution of DBCO-PEG4-NHS ester (Click Chemistry Tools; 0.0308 mL of 25 mM as determined by $\epsilon_{309}$=13,449 $M^{-1}$ $cm^{-1}$, 770 nmol, 2.4 equiv) in methanol. The resulting mixture was allowed to sit for 4 hours. TNBS assay indicated loss of 81% of the available amines on the derivatized hyaluronic acid. A parallel reaction using 1.2 equivalent of DBCO-PEG4-NHS ester resulted in consumption of 64% of the available amines. For purification, the two reactions were combined and dialyzed (12-14 k MWCO) against PBS, then 5% w/v NaCl, then twice against water, then once against methanol. The dialysis mixture was concentrated to dryness to give 2.6 mg of a white glassy solid. This material was dissolved in 1 mL of water to give a solution of 6.5 mM disaccharide and 0.31 mM DBCO based on $\epsilon_{309}$=13,448 $M^{-1}$ $cm^{-1}$, corresponding to a DBCO substitution of 4.8% and a yield of acylation of 71%.

Example 36

Preparation of Hyaluronic Acid Hydrogels

Hyaluronic acid hydrogels are prepared by crosslinking clyclooctyne-derivatized hyaluronic acid (Example 35) with diazide crosslinkers of formula (1) wherein m=0, X=O—CO—NH—$(CH_2CH_2O)_3CH_2CH_2N_3$, $R^1$=$PhSO_2$, $R^2$=H, one $R^5$=H and the other $R^5$=$(CH_2)_5N_3$. Gel formation is typically performed in water or buffered water using a 2:1 molar ratio of cyclooctyne to diazide crosslinker, optionally in the presence of a solution of protein or small molecule to be encapsulated.

To study diffusion of proteins from the hyaluronic acid hydrogel matrix, a stable hydrogel was prepared by mixing a solution (0.065 mL) of DBCO-HA (Example 35), 6.6% DS DBCO, 3.9 mM DBCO) in water with a solution of diazido-PEG of either MW=2000 or 5000 (0.005 mL of 25 mM, 0.5 equiv/DBCO). This hydrogel master mix 0.07 mL was immediately mixed with a protein or small molecule substrate solution (0.01 mL) for encapsulation in the bottom of a standard plastic 2.5 mL cuvette. The half-lives for diffusion from the gels are given in Table 2 below:

TABLE 2

| Substrate | Lys (DNP) | myoglobin | carbonic anhydrase | BSA | IgG |
|---|---|---|---|---|---|
| Mw | 312 | 18,000 | 29,000 | 66,000 | 150,000 |
| $t_{1/2}$ (2K gel) | 0.96 h | 3.98 h | 3.66 h | 4.26 h | 5.71 h |
| $t_{1/2}$ (5K gel) | 1.25 h | 3.14 h | 3.36 h | 3.65 h | 3.32 h |

Alternatively, drugs may be releasably linked to the hyaluronic acid prior to gel formation by reaction of a subset of the available cyclooctynes with azide-linker-drug as described in Example 29 and Example 32 above. In this case, the amount of diazide crosslinker used for gel formation is calculated based on the available cyclooctynes remaining after drug attachment. Attachment of 5-(aminoacetamido)fluorescein via a linker with $R^D$=(4-chlorophenyl)$SO_2$ provided a hyaluronic acid hydrogel that released AAF with $t_{1/2}$=49 h at pH 7.4, 37° C.

Example 37

Method for Preparing Hydrogels with Controlled Stoichiometries

As depicted in FIG. 11, commercially available S-t-Butylthio-cysteine (H Cys($^t$BuS)) is acylated with a cyclooctyne succinimidyl ester (e.g. DBCO—HSE or BCN—HSE) to give CO-Cys($^t$BuS)OH (A'=COOH; B=cyclooctyne; C=$^t$BuS). A 4-arm amino PEG (A=$NH_2$) is acylated (e.g., using a carbodiimide) with this CO-Cys(tBuS)OH to give the CO/tBuS-functionalized PEG. An azido-linker($R^{11}$)-drug is coupled to the cyclooctyne residues, then the tBuS group is removed, for example using a thiol such as dithiothreitol or with a phosphine such as TCEP, and the thiol-derivatized PEG is purified of small thiols (for example, using dialysis or gel filtration chromatography) and reacted with a cyclooctyne-maleimide, cyclooctyne-haloacetamide, or cyclooctyne-vinylsulfonamide to introduce exactly 4 cyclooctyne gelation sites per molecule. This intermediate is then crosslinked to form a hydrogel using a compound of formula (1) or (2) wherein the reactive functional groups are azide. Alternatively, the thiol-derivatized PEG (prior to reaction with cyclooctyne-maleimide) could also be polymerized with a compound of formula (1) or (2) wherein the reactive functional group is a Michael acceptor or alkylating agent such as maleimide, vinyl sulfone, vinyl sulfonamide, acrylate, acrylamide, haloacetate, or haloacetamide. Orthogonally protected adapters other than S-t-Butylthio-cysteine may similarly be used, for example suitably protected lysines, aspartates, or glutamates or synthetic adapters not based on amino-acids.

The invention claimed is:
1. A hydrogel that is biodegradable under physiological conditions which hydrogel comprises one or more polymers crosslinked by a linker that decomposes by a beta elimination reaction,
wherein said linker is a residue of formula (2)

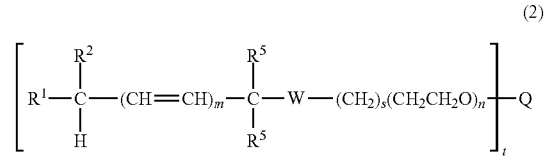

(2)

wherein at least two of said $R^1$, $R^2$, $R^3$ are coupled through functional groups to said one or more polymers;
m is 0 or 1;
n is 1-1000;
s is 0-2;
t is 2, 4, 8, 16 or 32;
Q is a core group having the valency t;
W is O(C=O)O, O(C=O)NH, O(C=O)S,

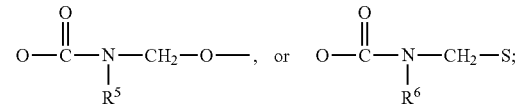

wherein $R^6$ is H, optionally substituted alkyl, optionally substituted aryl, optionally substituted heteroaryl, optionally substituted arylalkyl, or optionally substituted heteroarylalkyl;

wherein $R^1$ is CN or $SO_2R^3$, wherein
$R^3$ is H or optionally substituted alkyl;
aryl or arylalkyl, each optionally substituted;
heteroaryl or heteroarylalkyl, each optionally substituted; or
$OR^9$ or $NR^9_2$ wherein each $R^9$ is independently H or optionally substituted alkyl, or both $R^9$ groups taken together with the nitrogen to which they are attached form a heterocyclic ring; and wherein $R^2$ is H, alkyl, arylalkyl or heteroarylalkyl, each optionally substituted; or is CN or $NO_2$;
optionally substituted aryl;
optionally substituted heteroaryl;
optionally substituted alkenyl;
optionally substituted alkynyl;
$COR^3$ or $SOR^3$ or $SO_2R^3$ wherein
$R^3$ is H or optionally substituted alkyl;
aryl or arylalkyl, each optionally substituted;
heteroaryl or heteroarylalkyl, each optionally substituted; or
$OR^9$ or $NR^9_2$ wherein each $R^9$ is independently H or optionally substituted alkyl, or both $R^9$ groups taken together with the nitrogen to which they are attached form a heterocyclic ring;
$SR^4$ wherein
$R^4$ is optionally substituted alkyl;
aryl or arylalkyl, each optionally substituted; or
heteroaryl or heteroarylalkyl, each optionally substituted;
wherein $R^1$ and $R^2$ may be joined to form a 3-8 membered ring; and
each $R^5$ is independently H or is alkyl, alkenylalkyl, alkynylalkyl, $(OCH_2CH_2)_p$ O-alkyl wherein p=1-1000, aryl, arylalkyl, heteroaryl or heteroarylalkyl, each optionally substituted.

2. The hydrogel of claim 1 wherein each said functional group independently comprises $N_3$, $NH_2$, NH—$CO_2^tBu$, SH, $S^tBu$, maleimide, $CO_2H$, $CO_2^tBu$, 1,3-diene, cyclopentadiene, furan, alkyne, cyclooctyne, acrylate, or acrylamide; and wherein when one functional group comprises $N_3$ the other does not comprise alkyne or cyclooctyne; when one functional group comprises SH the other does not comprise maleimide, acrylate, or acrylamide; when one functional group comprises $NH_2$, the other does not comprise $CO_2H$; when one functional group comprises 1,3-diene or cyclopentadiene the other does not comprise furan.

3. The hydrogel of claim 1 wherein
$R^2$ is H; and/or
one of $R^3$ is H and the other is $(CH_2)_nZ$ wherein n is 1-6 and Z is a functional group to connect to said polymer.

4. The hydrogel of claim 1, wherein the polymer is of the formula $[—(CH_2)_s(CH_2CH_2O)_n]_tQ$, wherein
n is 10-1000;
s is 0-2;
t is 2, 4, 8, 16 or 32 and represents the number of arms of said polymer; and
Q is a core group having a valency=t,
and said polymer is coupled to said linkers through functional groups at the terminus of each of said arms.

5. The hydrogel of claim 4 wherein t is 4 and each arm of said polymer is terminated by two orthogonal functional groups.

6. The hydrogel of claim 4 wherein Q is pentaerythritol, tripentaerythritol, or hexaglycerin.

7. The hydrogel of claim 1, wherein in said cleavable crosslinking compound
m is 0,
n is 90-110,
s is 0,
t is 4,
W is O(C=O)NH,
Q is $C(CH_2)_4$,
$R^1$ is CN or $SO_2NR^3$, wherein $R^3$ is optionally substituted alkyl;
aryl or arylalkyl, each optionally substituted; or
heteroaryl or heteroarylalkyl, each optionally substituted;
$R^2$ and one of $R^5$ is H, and
the other $R^5$ is $(CH_2)_5N_3$.

8. The hydrogel of claim 1 which further comprises a drug.

9. The hydrogel of claim 8 wherein said hydrogel includes a residue of formula (3)

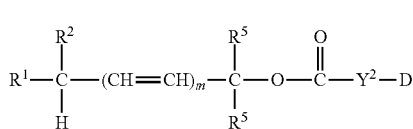

(3)

wherein at least one of $R^1$, $R^2$, $R^5$ is coupled to a polymer;
m is 0 or 1;
D is a drug or prodrug;
$Y^2$ is NH or $NBCH_2$ wherein B is H, alkyl, arylalkyl, heteroaryl, or heteroarylalkyl, each optionally substituted; and
wherein one and only one of $R^1$ and $R^2$ may be H or may be alkyl, arylalkyl or heteroarylalkyl, each optionally substituted;
at least one or both $R^1$ and $R^2$ is independently CN; $NO_2$;
optionally substituted aryl;
optionally substituted heteroaryl;
optionally substituted alkenyl;
optionally substituted alkynyl;
$COR^3$ or $SOR^3$ or $SO_2R^3$ wherein
$R^3$ is H or optionally substituted alkyl;
aryl or arylalkyl, each optionally substituted;
heteroaryl or heteroarylalkyl, each optionally substituted; or
$OR^9$ or $NR^9_2$ wherein each $R^9$ is independently H or optionally substituted alkyl, or both $R^9$ groups taken together with the nitrogen to which they are attached form a heterocyclic ring;
$SR^4$ wherein
$R^4$ is optionally substituted alkyl;
aryl or arylalkyl, each optionally substituted; or
heteroaryl or heteroarylalkyl, each optionally substituted;
wherein $R^1$ and $R^2$ may be joined to form a 3-8 membered ring; and
each $R^5$ is independently H or is alkyl, alkenylalkyl, alkynylalkyl, $(OCH_2CH_2)_p$ O-alkyl wherein p=1-1000, aryl, arylalkyl, heteroaryl or heteroarylalkyl, each optionally substituted.

10. The hydrogel of claim 9 wherein
the polymer is the residue of an 8-arm polyethylene glycol comprising a cyclooctyne group at the terminus of each arm wherein at least some of said arms have been coupled to

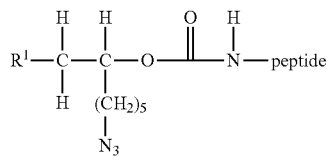

wherein $R^1$=CN; $NO_2$;
optionally substituted aryl;
optionally substituted heteroaryl;
optionally substituted alkenyl;
optionally substituted alkynyl;
$COR^3$ or $SOR^3$ or $SO_2R^3$ wherein
$R^3$ is H or optionally substituted alkyl;
aryl or arylalkyl, each optionally substituted;
heteroaryl or heteroarylalkyl, each optionally substituted; or
$OR^9$ or $NR^9{}_2$ wherein each $R^9$ is independently H or optionally substituted alkyl, or both $R^9$ groups taken together with the nitrogen to which they are attached form a heterocyclic ring; or
$SR^4$ wherein
$R^4$ is optionally substituted alkyl;
aryl or arylalkyl, each optionally substituted; or
heteroaryl or heteroarylalkyl, each optionally substituted.

* * * * *